United States Patent [19]

Kobayashi et al.

[11] Patent Number: 5,697,888
[45] Date of Patent: Dec. 16, 1997

[54] ENDOSCOPE APPARATUS HAVING VALVE DEVICE FOR SUPPLYING WATER AND GAS

[75] Inventors: Norio Kobayashi; Takao Yamaguchi, both of Hachioji, Japan

[73] Assignee: Olympus Optical Co., Ltd., Tokyo, Japan

[21] Appl. No.: 420,489

[22] Filed: Apr. 12, 1995

[30] Foreign Application Priority Data

Apr. 21, 1994 [JP] Japan ..................... 6-083205
Feb. 28, 1995 [JP] Japan ..................... 7-040254

[51] Int. Cl.[6] ........................................ A61B 1/12
[52] U.S. Cl. ................. 600/159; 600/157; 137/606
[58] Field of Search ..................... 137/240, 606; 251/367; 600/153–159

[56] References Cited

U.S. PATENT DOCUMENTS

| | | | |
|---|---|---|---|
| 3,903,877 | 9/1975 | Terada | 600/157 |
| 4,261,343 | 4/1981 | Ouchi et al. | 600/159 X |
| 4,408,598 | 10/1983 | Ueda | 600/159 |
| 4,892,112 | 1/1990 | Knetsch | 134/102.1 |
| 5,027,791 | 7/1991 | Takahashi | 600/159 X |
| 5,125,910 | 6/1992 | Freitas | 600/159 X |
| 5,313,934 | 5/1994 | Wiita et al. | |

FOREIGN PATENT DOCUMENTS

| | | |
|---|---|---|
| 62-30766 | 7/1987 | Japan . |
| 64-83241 | 3/1989 | Japan . |
| 2-131714 | 11/1990 | Japan . |
| 5-11841 | 3/1993 | Japan . |
| 5-103749 | 4/1993 | Japan . |

Primary Examiner—Richard J. Apley
Assistant Examiner—John Leubecker
Attorney, Agent, or Firm—Frishauf, Holtz, Goodman, Langer & Chick

[57] ABSTRACT

An endoscope apparatus having main body and an outer unit. The main body has an insertion section. The outer unit comprises an inner tube removably mounted on the insertion section and an inner tube removably mounted on the inner tube. A first passage is provided between the inner tube and the outer circumferential surface of the insertion section, and a second passage is provided between the inner tube and the outer tube. Liquid is supplied to and drawn from the distal end of the insertion section through one of the passages. Gas is applied onto the distal end of the insertion section through the other of the passages.

10 Claims, 14 Drawing Sheets

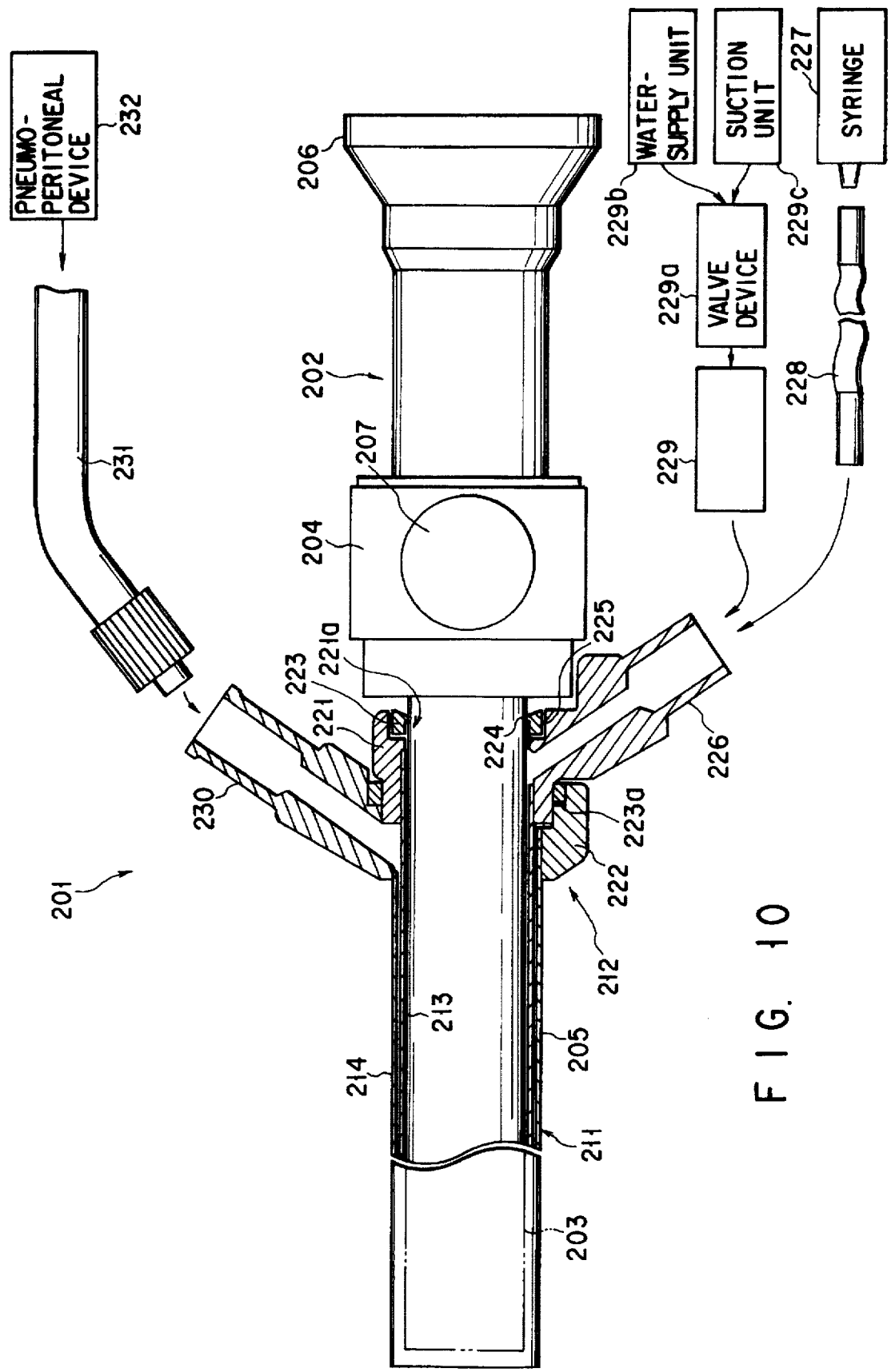
F I G. 10

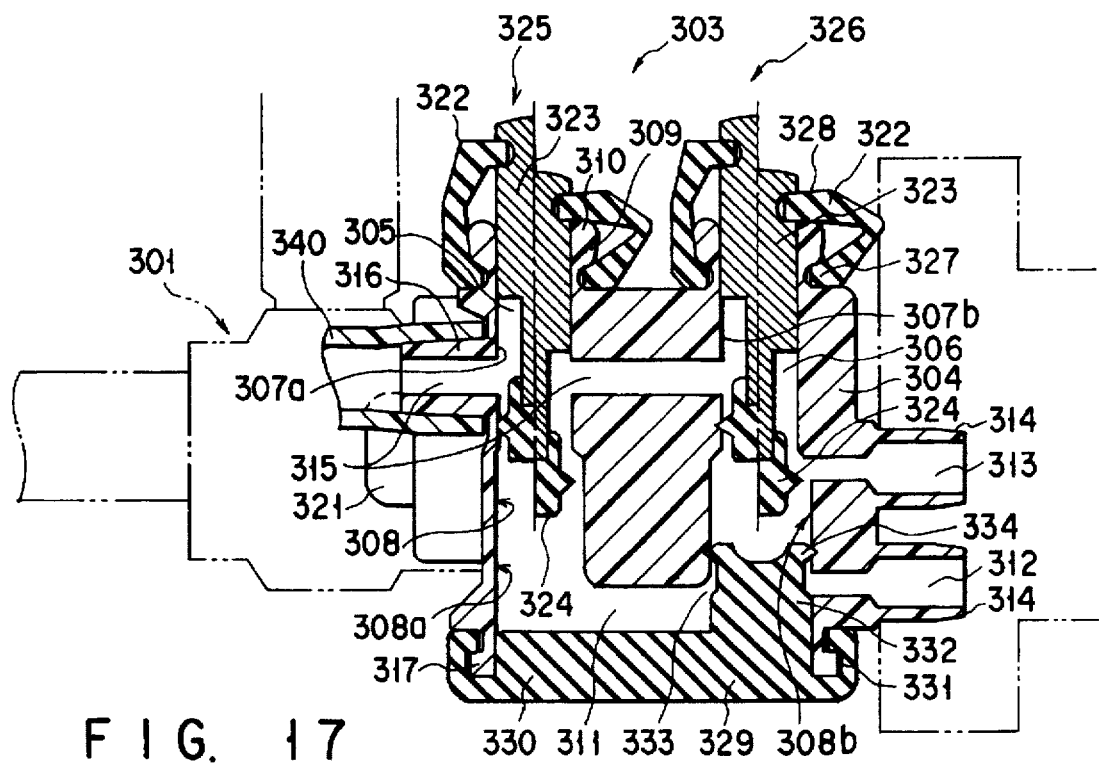
F I G. 17
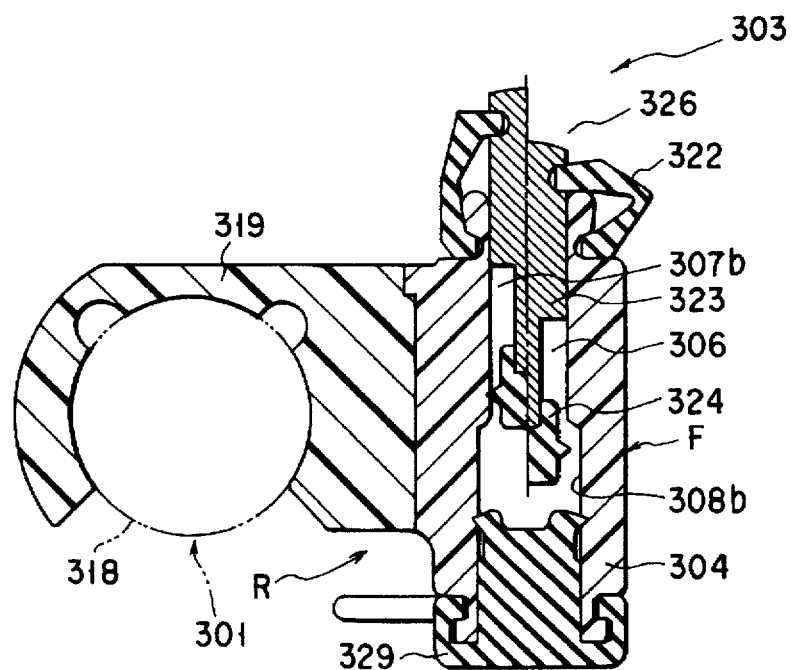
F I G. 18

ENDOSCOPE APPARATUS HAVING VALVE DEVICE FOR SUPPLYING WATER AND GAS

BACKGROUND OF THE INVENTION

1. Field of the Invention

The present invention relates to an endoscope apparatus for use in examining a body cavity and applying treatment in the body cavity.

2. Description of the Related Art

Various types of endoscopes are used in examining a body cavity of a patient and performing treatment in the cavity. During the use of an endoscope of any type, the insertion section of the endoscope remains in a body cavity and usually gets dirty with body fluid or the like. To provide a clear view, the observation window at the distal end of the insertion section must be kept clean as long as the endoscope is used.

In order to keep the observation window clean, the endoscope may be equipped with a washing sheath designed for use in combination with a rigidoscope, as is disclosed in Jpn. UM Appln. KOKOKU Publication No. 5-11841. Alternatively, the endoscope may be provided with a washing nozzle designed for use with a flexible scope, as is disclosed in Jpn. Pat. Appln. KOKAI Publication No. 5-103749, so that a washing water is applied from the nozzle onto the observation window, removing water drops or dirt from the window.

The observation window may be fogged, due to dew condensation resulting from a temperature difference between the body cavity and the distal end of the insertion section. When the window is fogged, the clearness of view will be deteriorated. To prevent such fogging of the observation window, a hydrophilic lubricant layer may be formed on the glass cover which is mounted on the distal end of the insertion section, as is disclosed in Jpn. UM Appln. KOKAI Publication No. 2-131714.

Further, as disclosed in Jpn. Pat. Appln. KOKAI Publication No. 62-83241, a heater may be used to heat the water in a water-supply unit connected to the endoscope, so that hot water may be applied onto the observation window, thereby not only to eliminate the fog on the window but also to remove water drops and dirt from the window.

Still further, as disclosed in Jpn. Pat. Appln. KOKOKU Publication No. 62-30766, a heating means such as a heater wire may be incorporated in the optical system (e.g., the objective lens) of the endoscope, to heat the objective lens, thereby to prevent the observation window from being fogged.

In the case of an endoscope of the type disclosed in Publications Nos. 5-11841 and 5-103749, when physiological saline at room temperature is supplied into a body cavity from the distal end of the insertion section, the temperature or humidity difference between the cavity and the distal end may become so great that dew is formed on the observation window. As a consequence, the observation window is fogged, impairing the clearness of view.

Once the clearness of view has been impaired, it is difficult for a surgeon to apply treatment in the body cavity by the use of the endoscope. He or she cannot help but wait until the fogging of the observation window ceases naturally. This inevitably lengthens the operation time. To clean the observation window to obtain a clear view, the surgeon may pull the insertion section out of the body cavity. This is time-consuming and inflicts pain on the patient.

The problem of window-fogging may be solved by heating the water-supply unit and applying hot water onto the observation window, as is proposed in Jpn. Pat. Appln. KOKAI Publication No. 62-83241. However, the water is cooled as it flows from the water-supply unit to the washing nozzle provided at the distal end of the insertion section. The water temperature may be lower than a desired value by the time it is applied onto the observation window, failing to eliminate the fog on the window. To avoid this, the water in the water-supply unit may be heated to a temperature much higher than the desired value. In this case, however, the hot water may burn body tissue as it flows through the water tube incorporated in the insertion section of the endoscope. In order to prevent such a burn, a device must be use which can maintain the washing water at a temperature almost the same as the patient's body temperature. The use of such a device increases the manufacturing cost of the endoscope. Furthermore, it is difficult to control the temperature of the hot water because of the heat loss at the water tube.

In an endoscope of the type disclosed in Jpn. UM Appln. KOKAI Publication No. 2-131714, the hydrophilic lubricant layer formed on the glass cover may be worn as the endoscope is repeatedly used or as the cover is repeatedly wetted with a sterilization solution.

In an endoscope of the type disclosed in Jpn. Pat. Appln. KOKOKU Publication No. 62-30766, the heating means (e.g., a heater wire) incorporated in the optical system such as the objective lens makes the endoscope complex and raises the manufacturing cost thereof.

SUMMARY OF THE INVENTION

In view of the foregoing, the object of the present invention is to provide an endoscope apparatus in which the fog on the observation window can easily be eliminated to shorten the time of an endoscope operation, which is yet simple in structure, and which can therefore be manufactured at low cost.

To attain the object, there is provided according to the invention an endoscope apparatus comprising a main body having an insertion section to be inserted into a body cavity and an operation section connected to the proximal end of the insertion section; an outer unit mounted on the main body; liquid-conducting means having a plurality of independent passages extending between the operation section and insertion section of the main body; and suction means for supplying liquids to a distal end of the insertion section through some of the passages of the liquid-conducting means and for drawing liquids from the distal end of the insertion section; and gas-supplying means for supplying a gas through the other passages of the liquid-conducting means, thereby to apply the gas onto the distal end of the insertion section.

Liquids supplied through some of the passages of the liquid-conducting means can be applied onto the distal end of the insertion section, removing foreign matter, if any, from the distal end. The distal end can be thereby washed clean. Further, the gas supplied through the other passages of the liquid-conducting means can be applied onto the distal end. Fog, if any on the distal end, can be thereby eliminated.

In case the distal end of the insertion section is stained with blood or the like, liquids are applied onto the distal end, washing the distal end, and then a dried gas is applied onto the distal end, eliminating or preventing the fog on the distal end. Thus, the distal end of the insertion section can be maintained clean without pulling the insertion section from the body cavity. This serves to shorten the time of an endoscope operation. In addition, the endoscope has a simple structure and can, therefore, be manufactured at low cost.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 10 is a cutaway view illustrating an endoscope apparatus according to a twelfth embodiment of the invention;

FIG. 17 is a longitudinal sectional view of a first modified valve device;

FIG. 18 is a cross-sectional view of the first modified valve device;

DETAILED DESCRIPTION OF THE PREFERRED EMBODIMENTS

An endoscope apparatus, which is the first embodiment of the invention, will now be described with reference to FIGS. 1 to 5 and FIGS. 6A to 6D.

Figure 1:
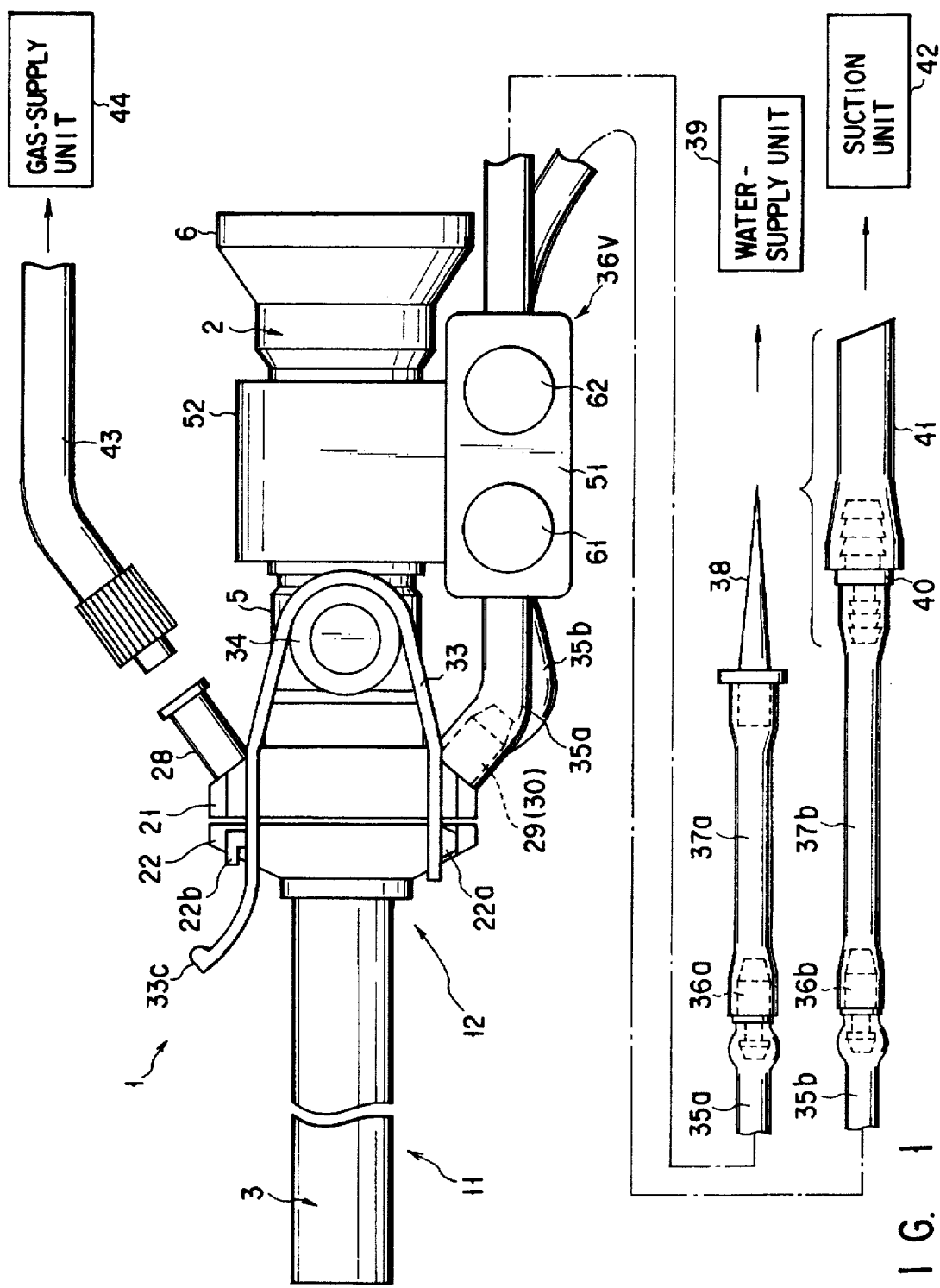
FIG. 1 is a schematic diagram of an endoscope apparatus according to a first embodiment of the present invention.
Figure 2:
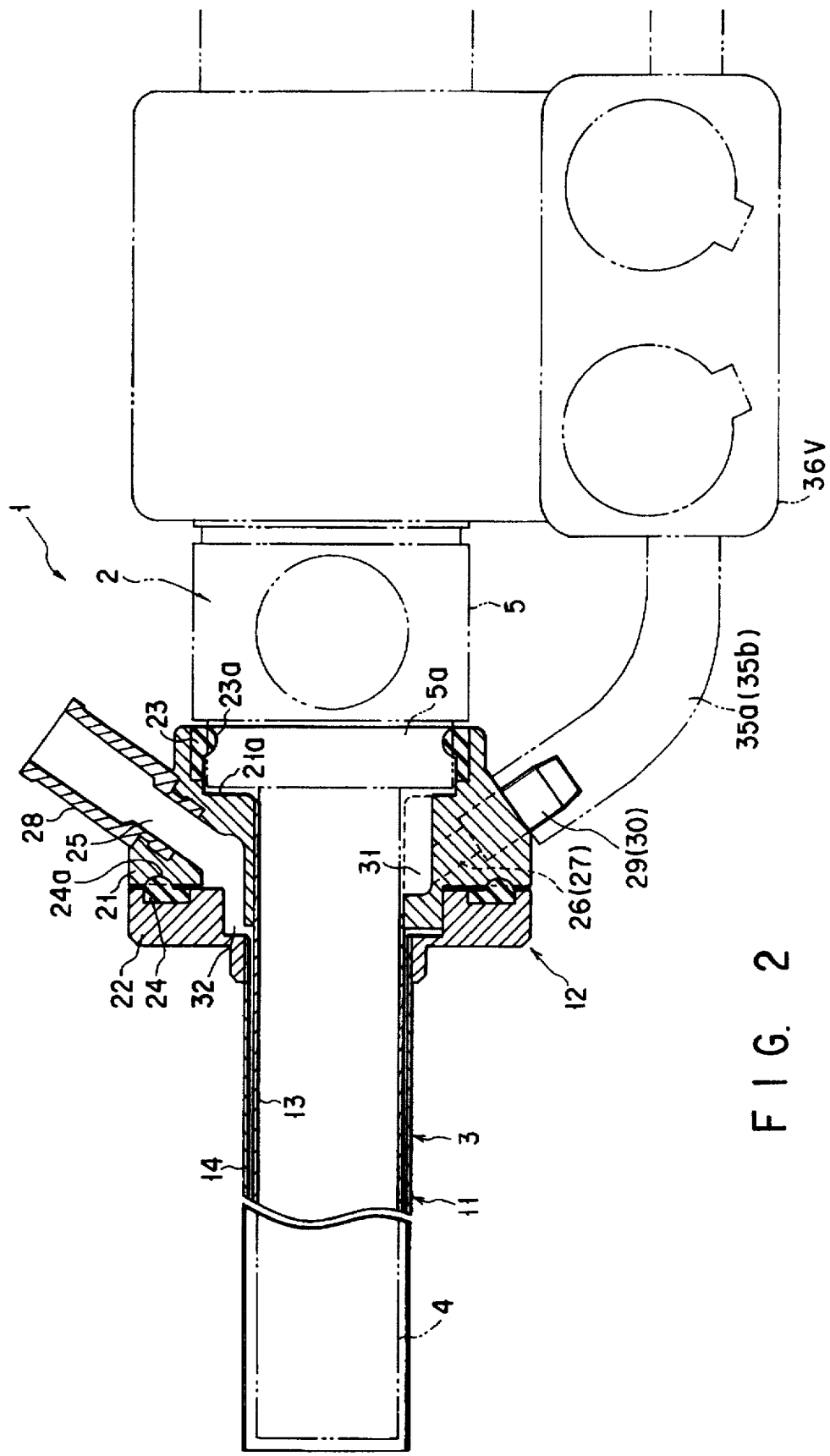
FIG. 2 is a longitudinal sectional view of the outer unit mounted on the main body of the endoscope apparatus shown in FIG. 1.
Figure 3:
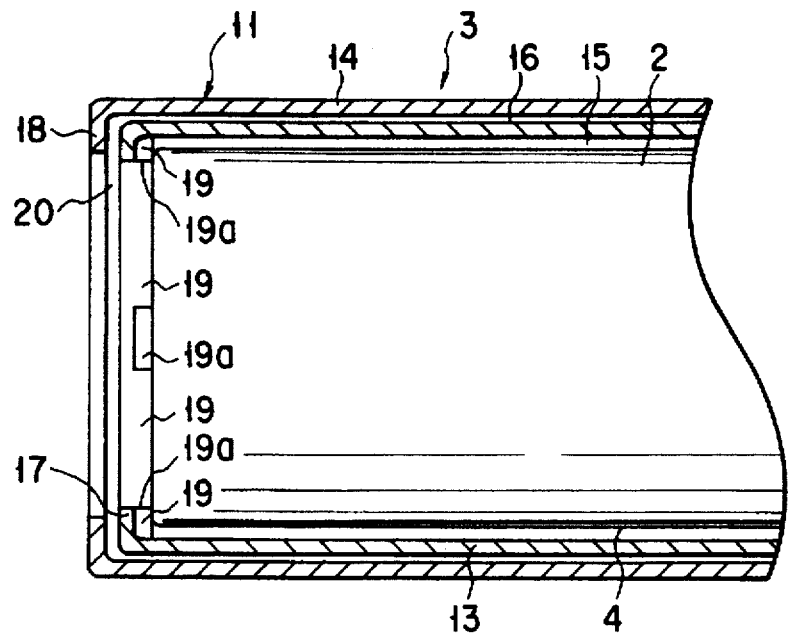
FIG. 3 is a longitudinal sectional view of the distal end portion of the outer unit.

As shown in FIG. 1, the endoscope apparatus 1 comprises a main body 2 and an outer unit 3 mounted on the main body 2. The main body 2 comprises an insertion section 4 and an operation section 5 as illustrated in FIG. 2. The insertion section 4 is to be inserted into a body cavity. The operation section 5 is coupled to the proximal end of the insertion section 4. As shown in FIG. 1, the operation section 5 has an ocular unit 6 and a light-guide connector 34. The outer unit 3 comprises a tubular sheath 11 and an annular member 12. The sheath 11 and the member 12 are mounted on the insertion 4 and operation section 5 of the main body 2, respectively. The sheath 11 comprises an inner tube 13 and an outer tube 14 which are coaxial to each other. The inner tube 13 is mounted on the insertion section 4, and the outer tube 14 on the inner tube 13.

The inner tube 13 has almost the same length as the insertion section 4 of the main body 2 and an inner diameter slightly greater than the outer diameter of the insertion section 4. The outer tube 14 has almost the same length as the inner tube 13 and has an inner diameter slightly greater than the outer diameter of the inner tube 13. As seen from FIG. 3, an annular space is provided between the inner circumferential surface of the inner tube 13 and the outer circumferential surface of the insertion section 4. This space functions as a first passage 15. Similarly, an annular space is provided between the outer circumferential surface of the inner tube 13 and the inner circumferential surface of the outer tube 14. This space serves as a second passage 16. These passages 15 and 16 constitute a fluid-conducting means which extends from the operation section 5 to the distal end of the insertion section 4.

A ring-shaped inner flange 17 is formed integral with the distal end of the inner tube 13. The inner flange 17 extends toward the axis of the inner tube 13, that is, at the right angles to the wall of the inner tube 13. An outer flange 18, ring-shaped, too, is formed integral with the distal end of the outer tube 14. The outer flange 18 extends toward the axis of the outer tube 14, that is, at the right angles to the wall of the outer tube 14. The inner flange 17 has at least one depression in the inner surface. In the present embodiment, the flange 17 has four depressions 19 which are spaced apart at angular intervals of about 90°. The depressions 19 oppose the distal end of the first passage 15, defining openings 19a for applying and drawing liquid.

The inner tube 13 and the outer tube 14 have such lengths that the inner flange 17 and the outer flange 18 are spaced apart, defining a space which communicates with the second passage 16. This space serves as a gas-supplying port 20.

As illustrated in FIG. 2, the annular member 12 of the outer unit 3 comprises two coaxial rings 21 and 22. The first ring 21 is located in front of the second connector 22. The first ring 21 is mounted on the proximal end portion of the inner tube 13. The second ring 22 is mounted on the proximal end portion of the outer tube 14.

The first ring 21 of the annular member 12 has a hole 21a having a diameter larger than that of the insertion section 4 of the main body 2. Fitted in this hole 21a is the stepped portion 5a defined at the junction between the insertion section 4 and the operation section 5. An annular seal 23 is mounted on the inner circumferential surface of the hole 21a. The seal 23 is made of elastic material such as silicone. The seal 23 has an annular projection 23a on its inner circumferential surface. The projection 23a has a cross section which is substantially semicircular. The seal 23 has its outer circumferential surface adhered to the inner circumferential surface of the hole 21a, achieving airtight sealing. Alternatively, an annular groove may be made in the inner circumferential surface of the hole 21a, and the outer peripheral portion of the seal 23 may be fitted in this annular groove, thereby to accomplish airtight sealing.

The first ring 21 of the annular member 12 has a gas-supplying port 25, a liquid-supplying port 26, and a suction port 27. The gas-supplying port is formed in the upper half of the ring 21 and extends slantwise. The liquid-supplying port 26 and the suction port 27 are formed in the lower half of the ring 21 and extend slantwise and parallel to each other. Three tubular caps 28, 29 and 30 are provided, fitted at one end in the gas-supplying port 25, the liquid-supplying port 26 and the suction port 27, respectively. The first ring 21 has a groove 31 cut in the inner circumferential surface. The groove 31 extends parallel to the axis of the first ring 21, connecting the inner ends of the liquid-supplying port 26, the suction port 27 and the first passage 15.

An annular seal 24 is mounted on the rear surface of the second ring 22. Like the annular seal 23, the seal 24 is made of elastic material such as silicone and has an annular projection 24a on its rear surface. The projection 24a has a cross section which is substantially semicircular. The seal 24 has its front surface adhered to the rear surface of the second ring 22, achieving airtight sealing. Alternatively, an annular groove may be made in the rear surface of the ring 22, and the front portion of the seal 24 may be fitted in this annular groove, thereby to accomplish airtight sealing.

Figure 4:
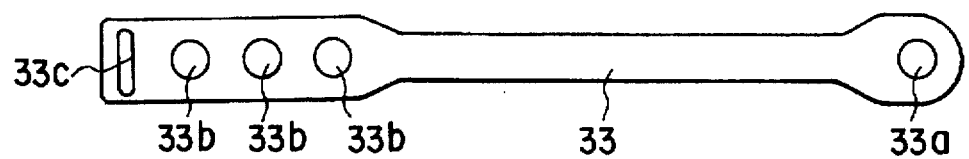
FIG. 4 is a plan view of the band for securing the outer unit to the main body.

The second ring 22 has a stepped portion at its inner circumferential surface, providing an annular passage 32 between the second ring 22 and the outer circumferential surface of the inner tube 13. The annular passage 32 connects the second passage 16 to the inner end of the gas-supplying port 25 of the first ring 21. The second ring 11 has a mushroom-shaped band holder 22a and an L-shaped hook 22b on its outer circumferential surface. The holder 22a holds the fastening band 33. The band 33 is either a long strip or a cord, made of elastic material such as silicone. As shown in FIG. 4, the band 33 has a thin intermediate portion. It has a hole 33a in one end portion and holes 33b and a friction member 33c in the other end portion.

To fasten the outer unit 3 to the main body 2, the band 33 is first connected to the holder 22a which is inserted in the hole 33a of the band 33. Next, the intermediate portion of band 33 is wrapped around the light-guide connector 34 of the operation section 5. The other end portion of the band 33 is then fastened to the hook 22b of the second ring 22, with the hook 22b inserted in one of the holes 33b. As a result, the band 33 secures the outer unit 3 to the main body 2. Since the fastening band 33 has a plurality of holes 33b in one end portion, it can serve to fasten the inner tube 13 to the main body 2, regardless of the type of the endoscope apparatus 1.

As shown in FIGS. 1 and 2, a first liquid-supplying tube 35a is connected at one end to the tubular cap 29, and a first suction tube 35b is connected at one end to the tubular cap 30. A valve device 36V is mounted on the middle portions of these tubes 35a and 35b. The valve device 36V is removably attached to the operation section 5 of the main body 2. The other end of the first liquid-supplying tube 35a is connected to one end of a connector 36a, and the other end of the first suction tube 35b to one end of a connector 36b. The other end of the connector 36a is connected to one end of a second liquid-supplying tube 37a. The second liquid-supplying tube 37a is connected at the other end to a water-supply unit 39 by a connector 38. The other end of the connector 36b is connected to one end of a second suction tube 37b. The second suction tube 37b is connected at the other end to one end of a connecting tube 41 by a connector 40. The other end of the connecting tube 41 is connected to a suction unit 42.

The first passage 15, i.e., the space between the inner tube 13 and the insertion section 4, functions as both a liquid-supplying passage and a suction passage. Through the first passage 15, liquid can be supplied to the distal end portion of the insertion section 4, and gas can be drawn from the distal end portion, thereby to remove foreign matter therefrom. On the other hand, the second passage 16, i.e., the space between the inner tube 13 and the outer tube 14, serves as a gas-supplying passage which is independent of the liquid-supplying passage and the suction passage. Through the gas-supplying passage, gas can be supplied to the distal end portion of the insertion section 4. The gas can then be applied onto the distal end of the section 4, so as to eliminate fogging, if any, on the observation window which is provided at the distal end of the insertion section.

The valve device 36V will be described in detail, with reference to FIGS. 5 and 6A. The device 36V comprises a main portion 51 and a connecting portion 52. The portion 52 is connected one side of the main portion 51 and has a cross section shaped like the letter of C. The portion 52 is removably coupled to a part of the main body 2 (for example, a portion close to the ocular unit 6 of the operation section 5. The connecting portion 52 has an inner diameter which is substantially equal to the outer diameter of the operation section 5. The portion 52 has a slit 52a, which has a width less than the outer diameter of the operation section 5. The connecting portion 52 is made of elastic material and can therefore undergo elastic deformation, broadening the slit 52a enough to hold a part of the operation section 5. Thus, the valve device 36V can be removably attached to the operation section 5 of the main body 2.

Figure 5:
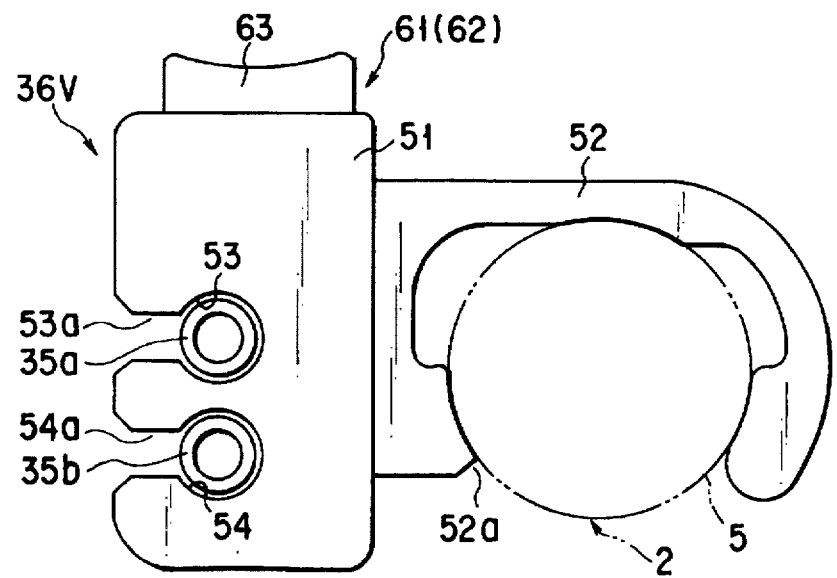
FIG. 5 is a plan view of the valve device incorporated in the endoscope apparatus shown in FIG. 1.

As shown in FIG. 5, the main portion 51 of the valve device 36V has two holes 53 and 54 which are spaced apart in vertical direction. The hole 53 guides the liquid-supplying tube 35a, while the hole 54 guides the suction tube 35b. Two slits 53a and 54a are formed on that side of the main portion 51 which faces away from the connecting portion 52. The slits 53a and 54a reach the holes 53 and 54, respectively. It is through these slits 53a and 54a that the liquid-supplying tube 35a and the suction tube 35b are pushed into and pulled from the holes 53 and 54. The slit 53a has a width less than the diameter of the hole 53, and the slit 54a has a width less than the diameter of the hole 54.

Figure 6A:
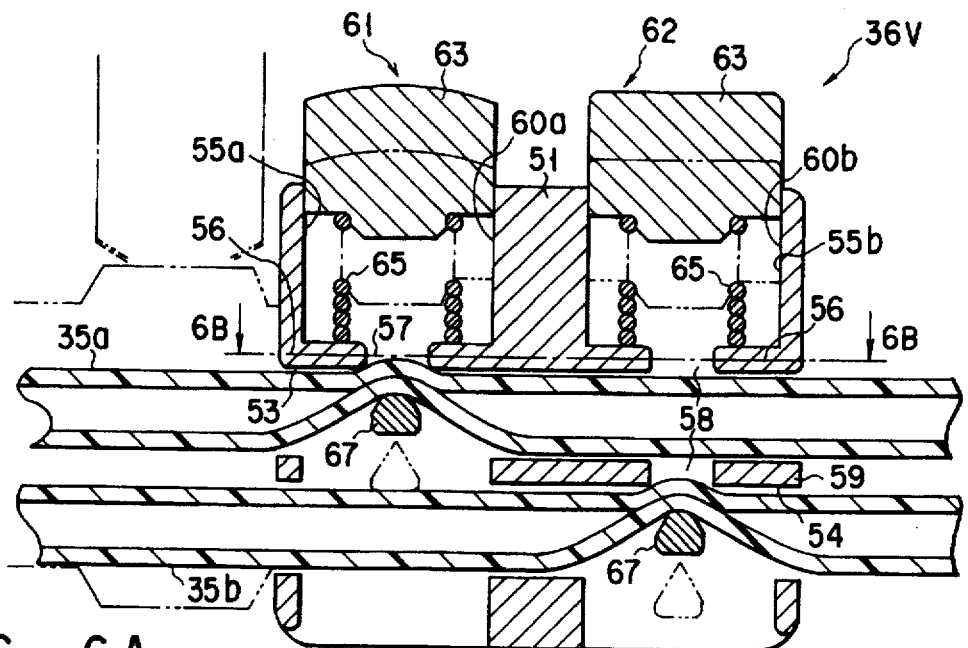
FIG. 6A is a longitudinal sectional view of the valve device.

As illustrated in FIG. 6A, the main portion 51 of the valve device 36V has two vertical holes 55a and 55b which extend at right angles to the holes 53 and 54 which guide the liquid-supplying tube 35a and the suction tube 35b. Two push buttons 61 and 62 are inserted in part in the vertical holes 55a and 55b, respectively. The button 61 can be moved up and down to open and close the liquid-supplying tube 35a. Similarly, the button 62 can be moved up and down to open and close the suction tube 35b.

The main portion 51 contains a first partition 56. The first partition 56 has two holes having the same diameter as the vertical holes 55a and 55b and axially aligned therewith. Located above the first partition 56 are the large-diameter portion 60a of the hole 55a and the large-diameter portion 60b of the hole 55b. The large-diameter portions 60a and 60b contain compression coil springs 65 for and 60b, respectively. The coil springs 65 abut at their upper end on the tops 63 of the buttons 61 and 62, biasing the buttons 61 and 62 upwards. The compression coil springs 65 may be replaced by elastic member made of rubber or the like.

Figure 6B:
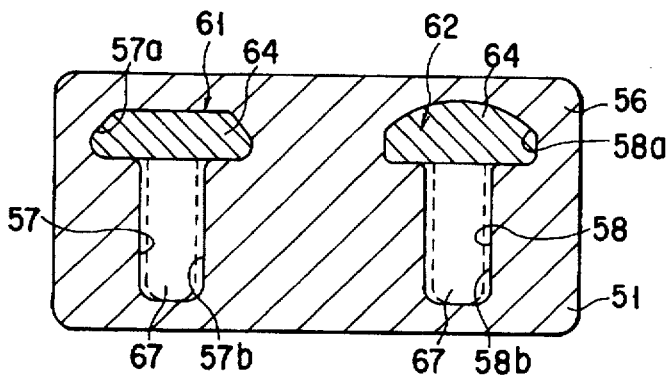
FIG. 6B is a sectional view of the valve device, taken along line 6B—6B.
Figures 6C, 6D:
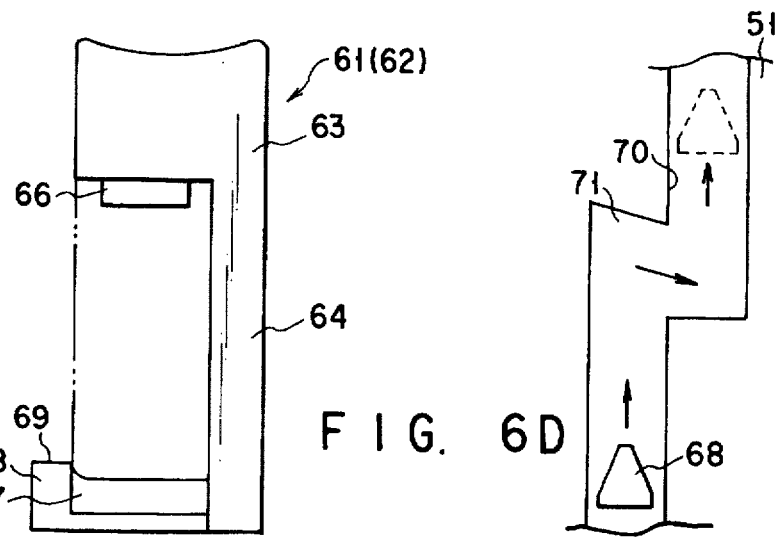
FIG. 6C is a side view of an operation button mounted on the valve device.
FIG. 6D is a longitudinal sectional view of the valve device, showing the arm-guiding groove formed in the valve device.

As shown in FIG. 6C, the buttons 61 and 62 have an operation arm 64 each. The arm 64 protrudes downwards from the top 63 of each push button. The arm 64 of the button 61 is longer than the arm 64 of the button 62. This is because the button 61 is used to open and close the liquid-supplying tube 35a, and the tube 35a is located below the suction tube 35b which is opened and closed by operating the button 62. Further, the buttons 61 and 62 have an L-shaped bar 67 each. The bar 67 horizontally extends from the lower end of the operation arm 64 and is a little longer than the diameter of the vertical hole. The distal end portion of the bar 67, which extends upwards, serves as a sliding member 68. The L-shaped bar 67 has a pointed end 69 gradually narrowing toward its top.

As illustrated in FIG. 6B, the first partition 56 has two T-shaped holes 57 and 58. The hole 57 consists of a first part 57a which allows the passage of the operation arm 64 of the first push button 61 for opening and closing the liquid-supplying tube 35a, and a second part 57b which allows the passage of the L-shaped bar 67 of the arm 64. Similarly, the hole 58 consists of a first part 58a which allows the passage of the operation arm 64 of the second push button 62 for opening and closing the suction tube 35b, and a second part 58b which allows the passage of the L-shaped bar 67 of the arm 64. While the second parts 57b and 58b of the holes 57 and 58 are identical in size and shape, the first parts 57a and 58b thereof are differ in size and shape. This is because the operation arms 64 of the push button 61 and 62 have different cross sections. Hence, the arm 64 of the first button 61 cannot pass through the part 58a of the hole 58, nor can the arm 64 of the second button 62 pass through the part 57a of the hole 57.

As FIG. 6A shows, the main portion 51 contains a second partition 59 which horizontally extends between the liquid-supplying tube 35a and the suction tube 35b. The second partition 59 has one T-shaped hole 58. This hole 58 is vertically aligned with the hole 58 made in the first partition 56; it consists of two parts 58a and 58b which are identical to the parts of the hole 58 of the first partition 56 and which allow the passage of the operation arm 64 and L-shaped bar 67 of the second push button 62.

The push buttons 61 and 62 have a positioning member 66 each, on the lower surface of the top 63. The member 66 protrudes downwards and fitted in the upper end of the compression coil spring 65, thus setting the spring 65 in axial alignment with the push button. Both compression coil springs 65 have their lower ends abutting on the upper surface of the first partition 56. The compression coil springs 65 bias the push buttons 61 and 62 outwards as illustrated in FIG. 6A. In this condition, the L-shaped bar 67 of the first push button 61 keeps closing the liquid-supplying tube 35a, and the L-shaped bar 67 of the second push button 62 keeps closing the suction tube 35b.

When the first push button 61 is depressed against the force of the coil spring 65 to the position indicated by the one-dash, two-dot line in FIG. 6A, its L-shaped bar 67 moves downwards, away from the liquid-supplying tube 35a. The tube 35a is thereby opened. Similarly, when the second push button 62 is pushed down against the force of the coil spring 65 to the position indicated by the one-dash, two-dot line in FIG. 6A, its L-shaped bar 67 moves downwards, away from the suction tube 35b. The suction tube 35b is thereby opened.

As shown in FIG. 6D, a crooked groove 70 is formed in one side of the vertical hole 55a in which the first push button 61 is inserted in part. The groove 70 extends vertically, for guiding the sliding member 68 of the push button 61. The groove 70 is positioned such that its crooked portion 71 is located above the first partition wall 56. The upper edge of the crooked portion 71 slopes downward. A similar crooked groove is formed in one side of the vertical hole 55b in which the second push button 62 is inserted in part.

As FIG. 1 shows, the tubular cap 28 is connected at the outer end to one end of a gas-supplying tube 43, the other end of which is connected to a gas-supply unit 44. A valve device similar to the valve device 36V may be provided on the gas-supplying tube 43.

It will now be explained how the endoscope apparatus 1 is used.

First, the insertion section 4 of the main body 2 is inserted into the inner tube 13 of the outer unit. Then, the insertion section 4 covered with the inner tube 13 is inserted into the outer tube 14. This done, the outer unit 3 is fastened to the main body 2 by the fastening band 33. More precisely, the bands 33 already held at one end by the holder 22a of the second ring 22 is pulled and wrapped around the light-guide connector 34 of the operation section 5. Then, the other end portion of the band 33 is fastened to the hook 22b of the second ring 22, by inserting the hook 22b in one of the holes 33b made in the other end portion of the band 33. The outer unit 3 having been fastened to the main body 2, the distal end of the insertion section 4 contacts the inner surface of the inner flange 17. The depressions 19 formed in the inner surface of the flange 17 oppose the distal end of the first passage 15, whereby the openings 19a for applying and drawing liquid are provided.

Next, the liquid-supplying tube 35a, the suction tube 35b, and the gas-supplying tube 43 are connected to the tubular caps 29, 30 and 28, respectively. The valve device 36V is attached to that part of the operation section 5 which is closed to the ocular unit 6. The the liquid-supplying tube 35a and the suction tube 35b are then fitted into the holes 53 and 54 of the valve device 36V, while both push buttons 61 and 62 on the valve device 36V are held depressed. After the tubes 35a and 35b have been properly set in the holes 53 and 54, respectively, the push buttons 61 and 62 are released. The compression coil springs 65 push the buttons 61 and 62 outwards. The L-shaped bar 67 of the first push button 61 presses the tube 35a onto the first partition 56, collapsing and closing the liquid-supplying tube 35a. Meanwhile, the L-shaped bar 67 of the second push button 62 presses the tube 53b onto the second partition 59, collapsing and closing the suction tube 35b.

While the endoscope apparatus 1 is being used to examine a body cavity, the distal end of the insertion section 4 may get dirty, inevitably impairing the clearness of view. To obtain a clear view again, the valve device 36V is operated in the following procedure. At first, the first push button 61 is pushed against the force of the compression coil spring 65. The the L-shaped bar 67 of the button 61 is moved down to the position indicated by the one-dash, two-dot line in FIG. 6A, leaving away from the liquid-supplying tube 35a. The liquid-supplying tube 35a is thereby opened.

Now that the liquid-supplying tube 35a is opened, the water supplied from water-supply unit 39 flows into the first passage 15 through the liquid-supplying port 26 and the groove 31 of the first ring 21. The water further flows through the first passage 15 into the Finally, it is applied from the openings 19a onto the distal end of the insertion section 4 of the main body 2. The dirt (e.g., body fluid and the like) is thereby removed from the distal end of the insertion section 4.

After the distal end of the insertion section 4 has been thus washed clean, the first push button 61 is released, whereby the compression coil spring 65 pushes the L-shaped bar 67 upwards. Thus pushed, the L-shaped bar 67 presses the liquid-supplying tube 35a onto the first partition 56, collapsing and closing the tube 35a. Then, the second push button 62 is pushed against the force of the compression coil spring 65. The the L-shaped bar 67 of the second button 62 is moved down, leaving away from the suction tube 35b. The suction tube 35b is thereby opened. As a result of this, the suction unit 42 is pneumatically connected to the body cavity by the first suction tube 35b, the second suction tube 37a and the connecting tube 41.

Once connected to the body cavity, the suction unit 42 applies a negative pressure into the body cavity. The water remaining at the distal end of the insertion section 4 and the dirt washed down therefrom are drawn into the first passage 15 through the openings 19a. The water and the dirt are further drawn from the groove 31 of the first ring 21 into the suction unit 42 through the suction port 27, the tubular cap 30, the suction tubes 35b and 37b and the connecting tube 41.

During the use of the endoscope apparatus 1, dews may be formed on the glass cover provided at the distal end of the insertion section 4, fogging the glass cover and deteriorating the clearness of view. To regain the view clearness, the gas-supply unit 44 is driven. The unit 44 supplies a gas into the second passage 16 through the tubular cap 28, the gas-supplying port 25 made in the first ring 21 and the annular passage 32 made in the second ring 22. The gas is then applied from the gas-supplying port 20 onto the distal end of the insertion section 4. The dews are blown away from the glass cover, eliminating the fogging on the glass cover and providing a clear view. The gas may be applied onto the distal end of the insertion section 4, either all time the endoscope apparatus 1 is used or only when necessary as has been described above.

The valve device 36V may be overhauled in the following procedure. First, the push buttons 61 and 62 are depressed. While keeping both buttons depressed, the liquid-supplying tube 35a and the suction tube 35b are removed from the holes 53 and 54 through the slits 53a and 54a. Next, the push buttons 61 and 62 are operated, moving the sliding members 68 along the crooked grooves 70 and removing them out of the grooves 70. Then, the push buttons 61 and 62 are pulled from the main portion 51 of the valve device 36V. The coil springs 65 can easily be pulled out since they are held by the positioning members 66 at only their upper ends.

Having the specific structure described above, the endoscope apparatus 1 is advantageous in the following respects.

When the outer unit 3 is attached to the main body 2, there are automatically formed the first passage 15 between the inner tube 13 of the unit 3 and the insertion section 4 of the main body 2, and also the second passage 16 between the inner tube 13 and outer tube 14 of the outer unit 3. The first passage 15 and the second passage 16 are independent of each other, not connected at all. Hence, a liquid can be applied through the first passage 15 onto the distal end of the insertion section 4 to wash down dirt (e.g., blood or the like) therefrom, and the dirt and the used liquid can be drawn from the body cavity into the suction unit 42 through the first passage 15.

Furthermore, a dried gas can be supplied through the second passage 16 into the gas-supplying port 20 (i.e., the space between the inner flange 17 and the outer flange 18), and is then applied the port 20 onto the distal end of the insertion section 4, blowing dews away from the glass cover and easily eliminating the fogging on the glass cover. Thus, it is possible to secure a clear view throughout the use of the endoscope apparatus 1, without pulling the insertion section 4 of the main body 2 from the body cavity.

Still further, the outer unit 3 is separated from the main body 2, having no components incorporated in the main body 2. It suffices to mount the outer unit 3 on the main body 2, only when necessary. The endoscope apparatus 1 is more simple in structure than in the case the components of the outer case 3 are incorporated in the main body 2. The endoscope apparatus 1 can therefore be manufactured at low cost.

Moreover, a dried gas may be supplied through the second passage 16 and applied from the gas-supplying port 20 onto the distal end of the insertion section 4, continuously all time the endoscope apparatus 1 is employed. In this case, the distal end of the insertion section 4 remains free of dew condensation. In other words, the distal end is reliably prevented from being fogged during the endoscope operation.

In addition, the outer unit 3 can be secured to the main body 2, merely by mounting the outer tube 14 on the main body 2 and fastening it to the main body 2 by means of the fastening band 33. When the outer tube 14 is thus fastened to the main body 2, the inner tube 13 is automatically secured to the main body 2. It is therefore easy to attach and secure the outer unit 3 to the main body 2. Since the fastening band 33 is made of elastic material, it can reliably attach the outer unit 3 to the main body 2, even if the components of the main body 2 or the outer unit 3, or both, have sizes different from the design values or are arranged at positions different from the prescribed ones. Further, since the fastening band 33 has a plurality of holes 33b each, and the hook 22b can be inserted in a selected one of these holes 33b, the outer unit 3 can be steadily attached to the main body 2, whichever position the light-guide connector 34 assumes with respect to the outer unit 3.

Furthermore, since the tubular caps 28, 29 and 30, all connected to the inner ring 21, extend slantwise with respect to the axis of the outer unit 3, the gas-supplying tube 43, the first liquid-supplying tube 35a and the first suction tube 35b can be connected to these caps 28, 29 and 30, respectively, more easily than otherwise.

As described above, the annular seal 23 made of elastic material (e.g., silicone) is mounted on the inner circumferential surface of the hole 21a of the first ring 21, and has an annular projection 23a which protrudes from the inner circumferential surface and which has a semicircular cross section. The outer circumferential surface of the seal 23 is adhered to the inner circumferential surface of the hole 21a, or the outer peripheral portion of the seal 23 is fitted in the annular groove made in the inner circumferential surface of the hole 21a, achieving airtight sealing. Similarly, the annular seal 24 made of elastic material (e.g., silicone) is mounted on the rear surface of the second ring 22, and has an annular projection 24a which protrudes from the rear surface and which has a semicircular cross section. The front surface of the seal 24 is adhered to the rear surface of the second ring 22, or the rear surface of the seal 24 is fitted in the annular groove made in the rear surface of the ring 22, thus accomplish airtight sealing. Hence, the seals 23 and 24 need not be removed to be washed, unlike O-rings or the like which may be used as seals.

As indicated above, the first passage 15, the liquid-supplying port 26 and the suction port 27 communicate with one another through the groove 31 made in the first ring 21, and the tubular caps 29 and 30 extend slantwise and backwards. Further, the gas-supplying port 25 made in the first ring 21 and the second passage 16 through the annular passage 32 made in the second ring 22, and the tubular cap 28 extends slantwise and backwards. Thus, the inner ring 14 can be, as a whole, more compact than the case where the tubular caps 28, 29 and 30 extend at right angles to the axis of the insertion section 4 of the main body 2. Since the tubular cap 28 is provided in the first ring 21, not in the second ring 22, the second ring 22 can be made shorter along its axis, and the outer tube 14 can have a longer effective length.

As mentioned above, the slits 53a and 54a are formed on one side of the main portion 51 of the valve device 36V. Through these slits 53a and 54a the liquid-supplying tube 35a and the suction tube 35b inserted sideways into the holes 53 and 54 of the main portion 52 and removed from the holes 53 and 54. Thus, the tubes 35a and 35b can be easily attached to and removed from the valve device 36V.

As shown in in FIG. 6B and described above, the second parts 57b and 58b of the holes 57 and 58 made in the first partition 56 are identical in size and shape, but the first parts 57a and 58b thereof are differ in size and shape. The operation arms 64 of the push button 61 and 62 have such different cross sections that the arm 64 of the button 61 can pass through the part 57a of the hole 57 but cannot pass through the part 58a of the hole 57, and that the arm 64 of the button 62 can pass through the part 58a of the hole 58 but cannot pass through the part 57a of the hole 57. Hence, the push buttons 61 and 62 cannot be placed in each other's position when the valve device 36V is assembled.

Furthermore, as described above, two crooked vertical grooves 70 respectively formed in one side of the vertical holes 55a and 55b, for guiding the sliding members 68 of the buttons 61 and 62 are positioned such that their crooked portions 71 are located above the first partition wall 56. Due to the positions of the crooked portions 71, the buttons 61 and 62 cannot be removed from the main portion 51 of the valve device 36V when the tubes 35a and 35b are removed from the man part 51, unless the sliding members 68 of the buttons 61 and 62 are moved along the grooves 70 to positions above the crooked portions 71. There is no possibility that the compression coil springs 65 push the buttons 61 and 62 out of the main portion 51.

Moreover, as described above, the L-shaped bars 67 of the buttons 16 and 62 have an pointed end 69 each. The pointed ends 69 prevent the liquid-supplying tube 35a and the suction tube 35b from the holes 53 and 54 of the main portion 51 through the slits 53a and 54a during the use of the valve device 36V.

Another endoscope apparatus, which is the second embodiment of the invention, will now be described with reference to FIG. 7A. This apparatus differs from the first embodiment in that the distal end portion of the outer unit 3 is modified as will be described below.

Figure 7A:
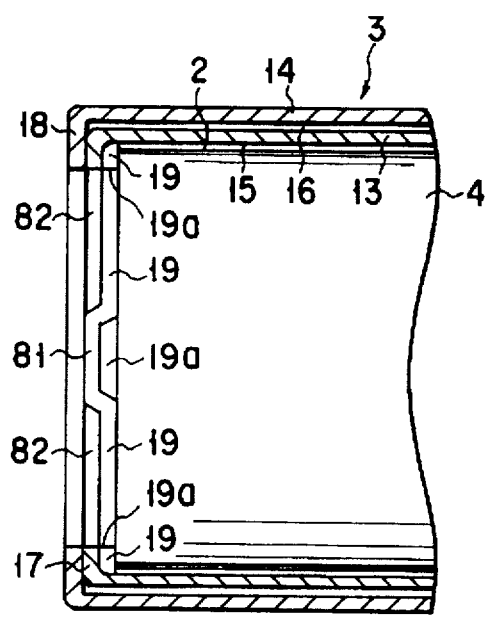
FIG. 7A is a longitudinal sectional view showing the main components of the outer unit of an endoscope according to a second embodiment of the invention.

As shown in FIG. 7A, the inner flange 17 has portions 81 which are plastically bent outwards. Each portion 81 define a depression which has almost the same depth as the depressions 19 formed in the inner surface of the flange 17. The outer flange 18 connected to the distal end of the outer tube 14 extends toward the axis of the outer tube 14, that is, at right angles to the wall of the outer tube 14. The outer flange 18 is flat, having neither depressions nor projections.

To fasten the outer unit 3 to the main body 2, the fastening band 33 connected at one end to the outer tube 14 are pulled, thereby moving the outer tube 14 toward the main body 2, while holding the bent portions 81 of the inner flange 17 in contact with the inner surface of the outer flange 18. As a result of this, the inner flange 17 is pressed, at its inner surface, onto the distal end of the insertion section 4. Then, spaces are provided between the other portions of the inner flange 17 than the portions 81, on the one hand, and the distal end of the insertion section 4, on the other hand. These spaces serve as openings 19a which communicate with the first passage 15 to apply and drawing a liquid. Since the portions 81 of the inner flange 17 abut on the inner surface of the outer flange 18, spaces are provided between the other portions of the inner flange 17, on the one hand, and the inner surface of the outer flange 18. These spaces function as gas-supply ports 82 which communicate with the second passage 16 to apply a gas.

When the outer flange 18 abuts on the inner flange 17 connected to the inner tube 13, the flanges 17 and 18 are automatically positioned with respect to each other, and the size of the gas-supply ports 82 communicating with the second passage 16 are automatically determined. Since the gas-supply ports 82 can be formed, only by bending some portions of the inner flange 17, both tubes 13 and 14 of the outer unit 3 have a simple structure. In addition, since the flanges 17 and 18 are formed by plastically processing tubes, the outer unit 3 comprises but a reduced number of components and can be manufactured at low cost.

Still another endoscope apparatus, which is the third embodiment of the invention, will be described with reference to FIG. 7B. The third embodiment differs from the first embodiment in that the distal end portion of the outer unit 3 is modified as will be explained below.

Figure 7B:
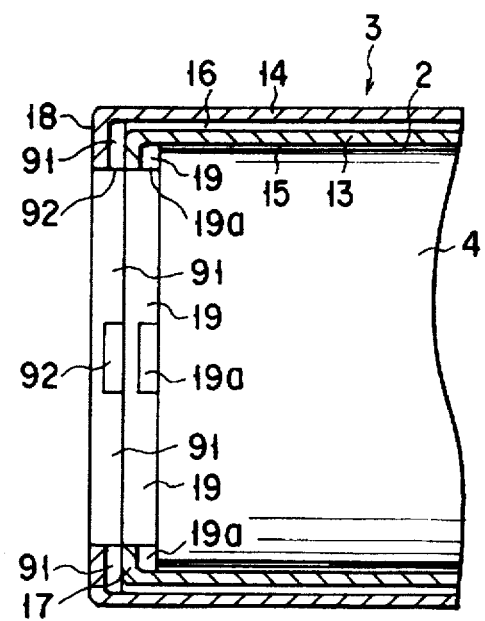
FIG. 7B is a longitudinal sectional view showing the main components of the outer unit of an endoscope according to a third embodiment of the invention.

As shown in FIG. 7B, the inner flange 17 connected to the distal end of the inner tube 13 has at least one depression 19 (or four depressions) its inner surface, and the outer flange 18 connected to the distal end of the outer tube 14 has at least one depression 91 (or four depressions) in its inner surface. When the inner tube 13 and the outer tube 14 are mounted on the main body 2, spaces are provided between the distal end of the insertions section 4 and the depressions 19 made in the inner surface of the inner flange 17 and serve as openings 19a which communicate with the first passage 15 to apply liquid onto the distal end of the insertion section 4 and draw it back into the first passage 15. At the same time, spaces are formed between the depressions 19 and the outer surface of the inner flange 17 and serve as gas-supply ports 92 which communicate with the second passage 16 to apply gas onto the distal end of the insertion section 4 and draw it into the second passage 16. The third embodiment achieves the same advantages as those of the second embodiment.

An endoscope apparatus, which is the fourth embodiment of this invention, will now be described with reference to FIG. 7C. The fourth embodiment differs from the first embodiment in that the distal end portion of the outer unit 3 is modified as follows.

Figure 7C:
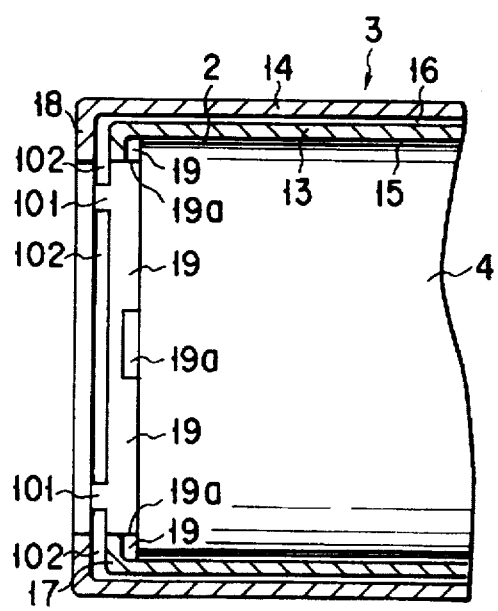
FIG. 7C is a longitudinal sectional view showing the main components of the outer unit of an endoscope according to a fourth embodiment of the invention.

As illustrated in FIG. 7C, the inner flange 17 connected to the distal end of the inner tube 13 has at least one depression 19 (or four depressions) its inner surface. The inner flange 17 further has at least two projections 101 on its outer surface. The outer flange 18 connected to the distal end of the outer tube 14 merely extends towards the axis of the outer tube 14, that is, at right angles to the wall of the outer tube 14. When the inner tube 13 and the outer tube 14 are mounted on the main body 2, spaces are provided between the distal end of the insertions section 4 and the depressions 19 made in the inner surface of the inner flange 17 and serve as openings 19a which communicate with the first passage 15 to apply liquid onto the distal end of the insertion section 4 and draw it back into the first passage 15. At the same time, the projections 101 abuts on the outer flange 18 connected to the distal end of the outer tube 14, and a space is formed between the outer surface of the inner flange 17 and the outer flange 18. This space communicates with the second passage 16 and functions as a gas-supply port 102 for applying gas onto the distal end of the insertion section 4 and drawing it into the second passage 16. The fourth embodiment has the same advantages as those of the second embodiment.

Another endoscope apparatus, which is the fifth embodiment of the present invention, will be described with reference to FIG. 7D. The fifth embodiment differs from the first embodiment in that the distal end portion of the outer unit 3 is modified as will be descried below.

Figure 7D:
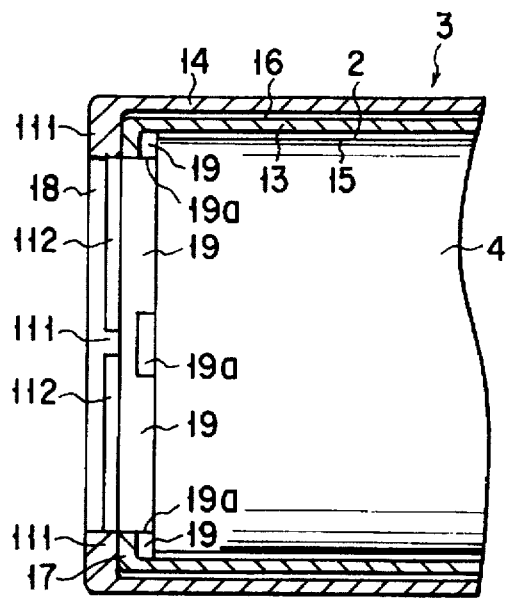
FIG. 7D is a longitudinal sectional view illustrating the main components of the outer unit of an endoscope according to a fifth embodiment of this invention.

As shown in FIG. 7D, the inner flange 17 connected to the distal end of the inner tube 13 has at least one depression 19 (or four depressions) its inner surface. The outer flange 18 connected to the distal end of the outer tube 14 has at least one projection 111 (or four projections) on its inner surface. When the inner tube 13 and the outer tube 14 are mounted on the main body 2, spaces are provided between the distal end of the insertions section 4 and the depressions 19 made in the inner surface of the inner flange 17 and serve as openings 19a which communicate with the first passage 15 to apply liquid onto the distal end of the insertion section 4 and draw it back into the first passage 15. Simultaneously, the projections 111 abuts on the inner flange 17, and a space is formed between the outer surface of the inner flange 17 and the outer flange 18. This space communicates with the second passage 16 and serves as a gas-supply port 112 for applying gas onto the distal end of the insertion section 4 and drawing it into the second passage 16. The fifth embodiment attains the same advantages as those of the second embodiment.

Figure 8A:
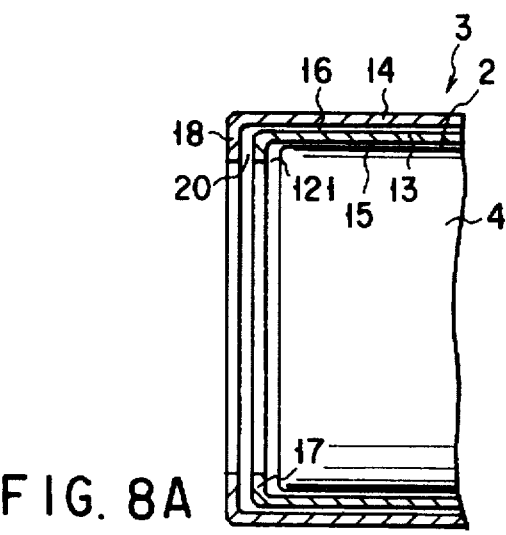
FIG. 8A is a longitudinal sectional view showing the main components of the outer unit of an endoscope according to a sixth embodiment of the present invention.

Still another endoscope apparatus, which is the sixth embodiment of the invention, will now be described with reference to FIG. 8A. The sixth embodiment differs from the first embodiment in that the distal end portion of the outer unit 3 is modified as follows.

When the inner tube 13 and the outer tube 14 are mounted on the main body 2, a space is defined between the distal end of the insertions section 4 and the inner flange 17 provided at the distal end of the inner tube 13. This space serves as an opening 121 which communicates with the first passage 15 to apply liquid onto the distal end of the insertion section 4 and draw it back into the first passage 15. Simultaneously, a space is provided between the outer surface of the inner flange 17 and the outer flange 18. This space communicates with the second passage 16 and serves as a gas-supply port 20 for applying gas onto the distal end of the insertion section 4 and drawing it into the second passage 16. The sixth embodiment, too, has the same advantages as those of the second embodiment.

Another endoscope apparatus, which is the seventh embodiment of the invention, will now be described with reference to FIG. 8B. The seventh embodiment differs from the first embodiment in that the distal end portion of the outer unit 3 is modified as follows.

Figure 8B:
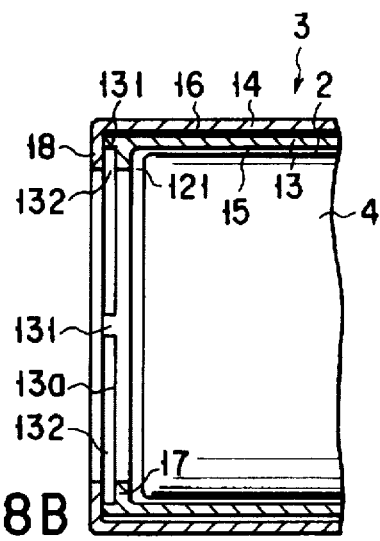
FIG. 8B is a longitudinal sectional view showing the main components of the outer unit of an endoscope according to a seventh embodiment of the invention.

As shown in FIG. 8B, the inner flange 17 provided at the distal end of the inner tube 13 has at least one projection 131 (or four projections) its outer surface. When the inner tube 13 and the outer tube 14 are mounted on the main body 2, a space is thereby provided between the distal end of the insertions section 4 and the inner flange 17 and serves as an opening 121 which communicates with the first passage 15 to apply liquid onto the distal end of the insertion section 4 and draw it back into the first passage 15. Simultaneously, the projections 131 abut on the outer flange 18 provided at the distal end of the outer tube 14, defining a space between the outer surface of the inner flange 17 and the outer flange 18. This space communicates with the second passage 16 and serves as a gas-supply port 132 for applying gas onto the distal end of the insertion section 4 and drawing it into the second passage 16. The seventh embodiment achieves the same advantages as those of the second embodiment.

Another endoscope apparatus, which is the eighth embodiment of the invention, will be described with reference to FIG. 8C. The eighth embodiment differs from the first embodiment in that the distal end portion of the outer unit 3 is modified as will be descried below.

Figure 8C:
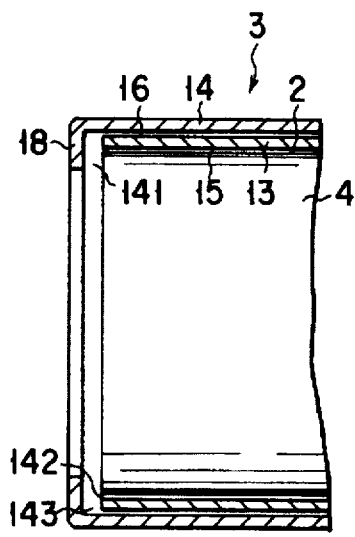
FIG. 8C is a longitudinal sectional view illustrating the main components of the outer unit of an endoscope according to an eighth embodiment of the invention.

As illustrated in FIG. 8C, no inner flange 17 is provided at the distal end of the inner tube 13. Only a flange 18 is connected to the distal end of the outer tube 14. When the inner tube 13 and the outer tube 14 are mounted on the main body 2, the distal end of the inner tube 13 is aligned with that of the insertion section 4, in a plane perpendicular to the axis the insertion section 4. At the same time, two spaces are provided between the inner surface of the flange 18. The first space communicates with the first passage 15 and serves as an opening 142 for applying liquid onto the distal end of the insertion section 4 and drawing it into the first passage 15. The second space communicates with the second passage 16 and serves as gas-supply port 143 for applying gas onto the distal end of the insertion section 4 and drawing it into the second passage 16. The eighth embodiment achieves the same advantages as those of the second embodiment.

Still another endoscope apparatus, which is the ninth embodiment of the present invention, will be described with reference to FIG. 8D. The ninth embodiment differs from the first embodiment in that the distal end portion of the outer unit 3 is modified as follows.

Figure 8D:
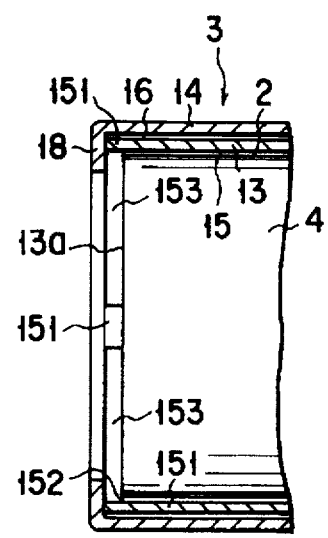
FIG. 8D is a longitudinal sectional view showing the main components of the outer unit of an endoscope according to a ninth embodiment of the invention.

As seen from FIG. 8D, no inner flange 17 is provided at the distal end 13a of the inner tube 13. Instead, at least one projection 151 (or four projections) is provided, protruding forward the distal end 13a. Only a flange 18 is connected to the distal end of the outer tube 14. When the inner tube 13 and the outer tube 14 are mounted on the main body 2, the distal end 13a of the inner tube 13 is aligned with that of the insertion section 4, in a plane perpendicular to the axis the insertion section 4. At this time, the projections 151 abut on the inner surface of the flange 18, whereby two spaces are provided between the inner surface of the flange 18. The first space communicates with the first passage 15 and serves as an opening 152 for applying liquid onto the distal end of the insertion section 4 and drawing it into the first passage 15. The second space communicates with the second passage 16 and serves as gas-supply port 153 for applying gas onto the distal end of the insertion section 4 and drawing it into the second passage 16. The ninth embodiment achieves the same advantages as those of the second embodiment.

Another endoscope apparatus, which is the tenth embodiment of the present invention, will be described with reference to FIG. 8E. The tenth embodiment differs from the first embodiment in that the distal end portion of the outer unit 3 is modified as will be described below.

Figure 8E:
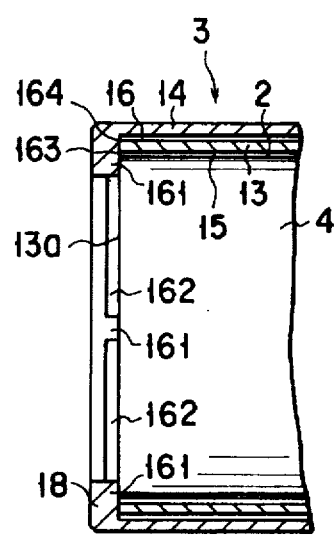
FIG. 8E is a longitudinal sectional view showing the main components of the outer unit of an endoscope according to a tenth embodiment of this invention.

As shown in FIG. 8E, no inner flange 17 is provided at the distal end 13a of the inner tube 13. Only a flange 18 is connected to the distal end of the outer tube 14. At least one projection 161 (or four projections) is provided, protruding backward from the inner surface of the flange 18. When the inner tube 13 and the outer tube 14 are mounted on the main body 2, the distal end 13a of the inner tube 13 is aligned with that of the insertion section 4, in a plane perpendicular to the axis the insertion section 4. At this time, the projections 161 abut on the distal end of the insertion section 4 and also on the distal end 13a of the inner tube 13, providing a space 162 between the flange 18 and the distal end of the insertion section 4. This space 162 communicates with an opening 162 communicating with the first passage 15 to apply liquid onto the distal end of the insertion section 4 and draw it back into the first passage 15. The space 162 also communicates with a gas-supply port 164 communicating with the second passage 16 to to apply gas onto the distal end of the insertion section 4 and draw it back into the second passage 16. The tenth embodiment achieves the same advantages as those of the second embodiment.

Still another endoscope apparatus, which is the eleventh embodiment of the invention, will be described with reference to FIG. 9. The eleventh embodiment differs from the first embodiment in that the distal end portion of the outer unit 3 is modified as will be described below.

Figure 9:
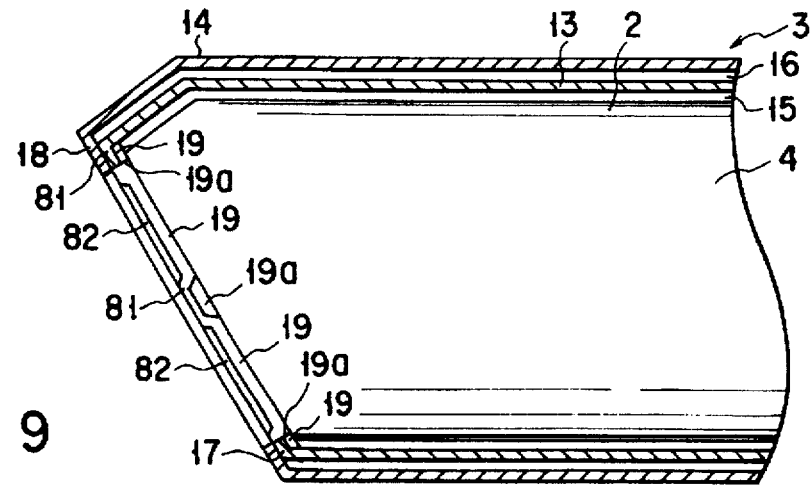
FIG. 9 is a longitudinal sectional view showing the main components of the outer unit of an endoscope according to an eleventh embodiment of the present invention.
Figure 11:
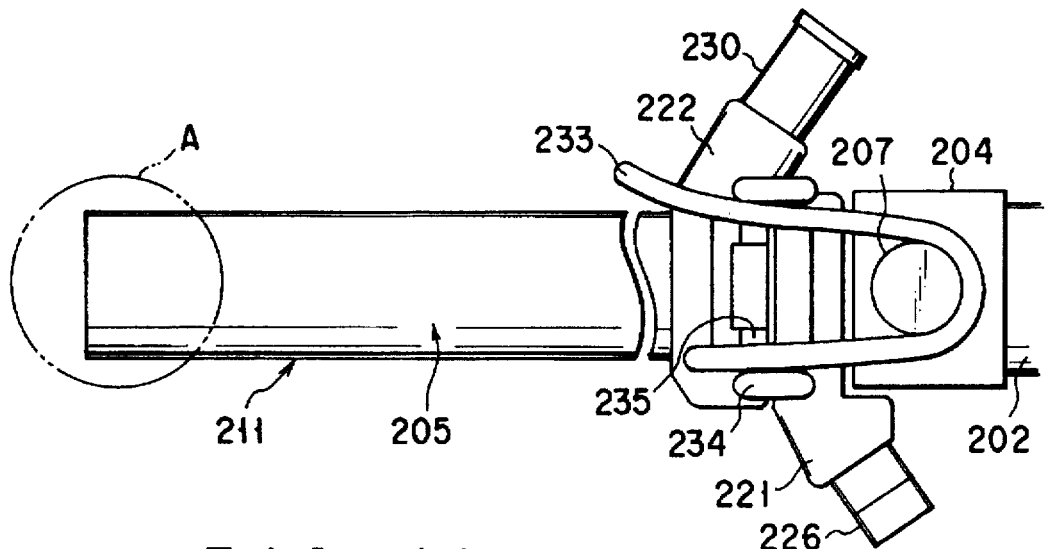
FIG. 11 is a side view of the apparatus shown in FIG. 10.
Figure 12:
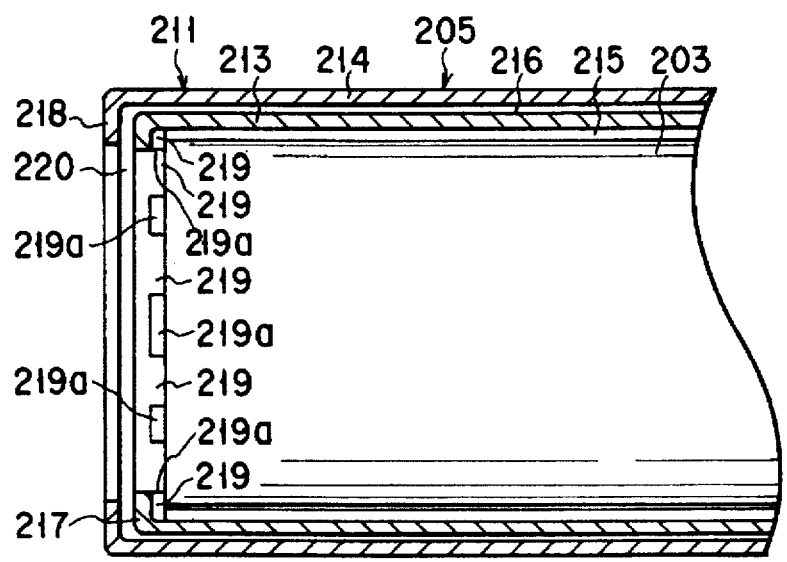
FIG. 12 is an enlarged, sectional view of the part A of the apparatus shown in FIG. 10.

As shown in FIG. 9, the inner flange 17 connected to the distal end of the outer tube 13 is inclined to the axis of the outer tube 13, thus extending along the inclined distal end of the insertion section 4. The inner flange 17 has some portions 81 plastically bent outwards, each defining a depression which has almost the same depth as the depressions 19 formed in the inner surface of the flange 17. The outer flange 18 connected to the distal end of the outer tube 14 extends slantwise along the inclined distal end of the insertion section 4. The outer flange 18 is flat, having neither depressions nor projections.

To fasten the outer unit 3 to the main body 2, the fastening band 33s connected at one end to the outer tube 14 are pulled, thereby moving the outer tube 14 toward the main body 2, while holding the bent portions 81 of the inner flange 17 in contact with the inner surface of the outer flange 18. The inner flange 17 is thereby pressed, at its inner surface, onto the distal end of the insertion section 4. Then, spaces are provided between the other portions of the inner flange 17 than the portions 81, on the one hand, and the distal end of the insertion section 4, on the other hand. These spaces serve as openings 19a which communicate with the first passage 15 to apply liquid onto the distal end of the section 4 and draw it back into the first passage 15. The portions 81 abut on the inner surface of the outer flange 18, providing spaces between the outer surface of the inner flange 17 and the inner surface of the outer flange 18. These spaces function as gas-supply ports 82 which communicate with the second passage 16 to apply a gas onto the distal end of the insertion section 4 and draw it into the second passage 16. The eleventh embodiment attains the same advantages as those of the second embodiment.

FIGS. 10 to 13 and FIGS. 14A to 14F shows an endoscope apparatus according to the twelfth embodiment of the present invention.

As illustrated in FIG. 10 which is a cutaway view, this endoscope apparatus 210 comprises a main body 202 and an outer unit 205 mounted on the main body 202. The main body 202 comprises an insertion section 203 and an operation section 204. The insertion section 203 is to be inserted into a body cavity. The operation section 204 is coupled to the proximal end of the insertion section 203. The operation section 5 has an ocular unit 206 and a light-guide connector 207. The outer unit 205 comprises a tubular sheath 211 and an annular member 112. The sheath 211 is mounted on the insertion section 203 of the main body 202, and the annular member 212 on the operation section 204 of the main body 2. The sheath 211 comprises an inner tube 213 and an outer tube 214 which are coaxial to each other. The inner tube 213 is mounted on the insertion section 203, and the outer tube 214 on the inner tube 213.

The inner tube 213 has almost the same length as the insertion section 203 of the main body 2 and an inner diameter slightly greater than the outer diameter of the insertion section 203. The outer tube 214 has almost the same length as the inner tube 213 and has an inner diameter slightly greater than the outer diameter of the inner tube 213. As seen from FIG. 12, an annular space is provided between the inner circumferential surface of the inner tube 213 and the outer circumferential surface of the insertion section 203. This space functions as a first passage 215. Similarly, an annular space is provided between the outer circumferential surface of the inner tube 213 and the inner circumferential surface of the outer tube 214. This space serves as a second passage 216. These passages 215 and 216 constitute a fluid-conducting means which extends from the operation section 204 to the distal end of the insertion section 203.

A ring-shaped inner flange 217 is formed integral with the distal end of the inner tube 213. The inner flange 217 extends toward the axis of the inner tube 213. In other words, the flange 217 extends at the right angles to the wall of the inner tube 213. An outer flange 218, ring-shaped, too, is formed integral with the distal end of the outer tube 214. The outer flange 218 extends toward the axis of the outer tube 214, namely at the right angles to the wall of the outer tube 214. The inner flange 217 has at least one depression 219 (or eight depressions) in the inner surface (i.e., the back), spaced apart at angular intervals of about 45°. The distal end of the insertion section 203 and the inner surface of the inner flange 217 are set in mutual contact. Hence, the depressions 219 define openings 219a which communicate with the first passage 215 to apply liquid onto the distal end of the insertion section 203 and draw it back into the first passage 215.

The inner tube 213 and the outer tube 214 have such lengths that the inner flange 217 and the outer flange 218 are spaced apart, defining a space which communicates with the second passage 216. This space serves as a gas-supplying port 220.

The inner tube 213 and the outer tube 214 have such lengths that an appropriate space is provided between the outer surface (i.e., the front) of the inner flange 17 and the inner surface (i.e., the back) of the outer flange 18. This space serves as a gas-supply port 220 which communicates with the second passage 216. The second passage 216 has a cross section large enough to accomplish pneumoperitoneal treatment. To be more specific, the cross section is preferably 1 mm$^2$ to 40 mm$^2$.

As shown in FIG. 10, the annular member 212 of the outer unit 205 comprises two coaxial rings 221 and 222. The first ring 221 is located in front of the second connector 222. The first ring 221 is mounted on the proximal end portion of the inner tube 213. The second ring 222 is mounted on the proximal end portion of the outer tube 214. These rings 221 and 222 are made of material (e.g., resin) which is easy to mold, and connected to the inner tube 213 and the outer tube 214, respectively, by means of outsert molding.

The first ring 221 has a hole 221a made in its rear end and having a diameter larger than the inner diameter of the ring 221, defining an annular space around the outer circumferential surface of the insertion section 203. Fitted in this annular space is an annular seal 223 which is an O-ring made of elastic material such as silicone. The seal 223 has an annular projection 224 on its inner circumferential surface. The projection 224 has a cross section which is substantially semicircular or U-shaped. The seal 223 has its outer circumferential surface adhered to the inner circumferential surface of the hole 221a, achieving airtight or watertight sealing. Alternatively, an annular groove may be made in the inner circumferential surface of the hole 221a, and the outer peripheral portion of the seal 223 may be fitted in this annular groove, thereby to accomplish airtight or watertight sealing.

A tubular cap 226 is formed integral with the first ring 221, communicating with the first passage 215. Preferably, the tubular cap 226 is shaped like a lure. The tubular cap 226 is connected to a commercially availably syringe 227, either directly or by a commercially available extension tube 228. Alternatively, the tubular cap 226 may be connected to a valve device 229a by a tube 229. Connected to the valve device 229a are a water-supply unit 229b and a suction unit 229c. The valve device 229a is operated to connect the water-supply unit 229b or the suction unit 229c to the tubular cap 226. It is desirable that the cap 226 extend slantwise and backwards, at an appropriate angle to the axis of the insertion section 203 of the main body 202.

An annular seal 223a is fitted in the rear end the second ring 222 in the same way as the annular seal 223 is fitted in the rear end of the first ring 221, accomplishing airtight or watertight sealing. A tubular cap 230 is formed integral with the second ring 222, communicating with the second passage 216. Like a commercially available cap for use in combination with a trocar, the tubular cap 230 is preferably shaped like a lure. The tubular cap 230 is connected by a connecting tube 231 to a pneumoperitoneal device 232. It is desirable that this tubular cap 230 be different in shape from the tubular cap 226 used to supply and draw water.

Figure 14A:
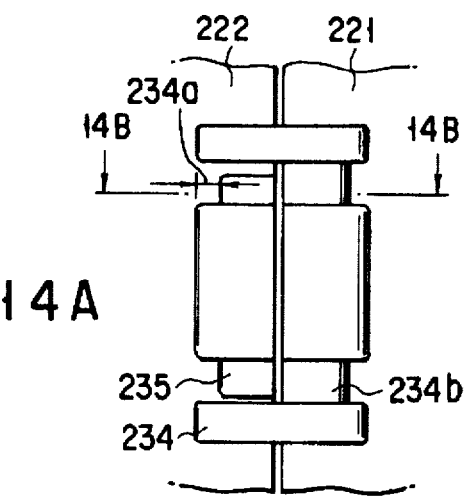
FIG. 14A is a front view of the rings used in the twelfth embodiment.
Figure 14C:
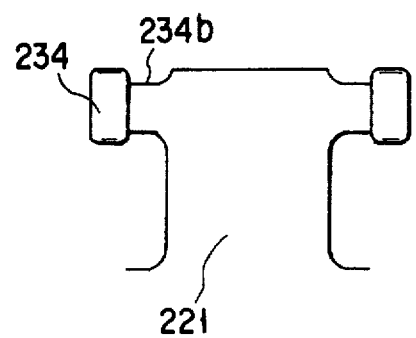
FIG. 14C is a side view of one of the rings.
Figure 14B:
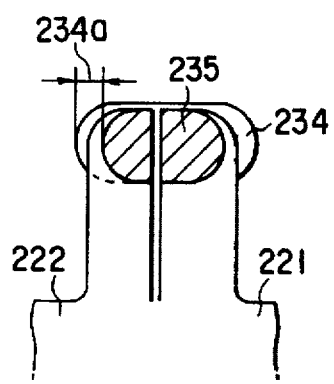
FIG. 14B is a sectional view taken along line 14B—14B shown in FIG. 14A.

The first ring 221 has at least one hook 234 (or two hooks) for holding a fastening band 233 which is used to fasten the outer unit 205 to the main body 202. As shown in FIG. 11 and FIGS. 14A to 14C, each hook 234 has a neck 234b around which the band 233 is wrapped. As is shown in FIG. 14C, the hooks 234 are T-shaped and connected to the sides of the first ring 221. The second ring 222 has projections 235 protruding from the sides. The projections 235 are shaped such that when they are connected to the hooks 234, the hooks 234 extend outwards, each defining a step 234a with the hook 234 as illustrated in FIGS. 14A and 14B.

Figure 13:
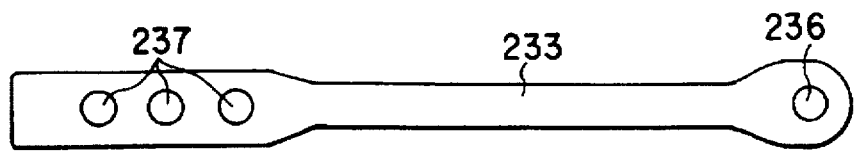
FIG. 13 is a plan view of a band for securing an outer unit to the main body of the apparatus shown in FIG. 10.

The fastening bands 233 are either long strips or cords, made of elastic material such as silicone. As shown in FIG. 13, each band 233 has a thin intermediate portion. It has a hole 236 in one end portion and holes 237 in the other end portion.

To fasten the inner tube 213 to the main body 202, the fastening band 33 is first connected to one of the hooks 234, with the hook 234 inserted in the hole 236 made in the band 233. Next, the band 233 is wrapped around the light-guide connector 207 of the operation section 204. The other end portion of the band 233 is then fastened to the other hook 234 of the first ring 221, with this hook 234 inserted in one of the holes 237 made in the band 233. As a result, the band 233 secures the inner tube 213 to the main body 202. Since the fastening band 233 has a plurality of holes 237 in one end portion, it can serve to fasten the inner tube 213 to the main body 202, regardless of the type of the endoscope apparatus 201.

To fasten both the inner tube 213 and the outer tube 214 to the main body 202, the fastening band 33 is first connected to one of the projections 235 of the second ring 222, with this projection 235 inserted in the hole 236 made in the band 233. Then, the band 233 is wrapped around the light-guide connector 207, and the other end portion of the band 233 is fastened to the other projection 235 the second ring 222, with this hook 235 inserted in one of the holes 237 of the band 233. In this case, the band 233 secures both tubes 213 and 214 to the main body 202.

Figure 14D:
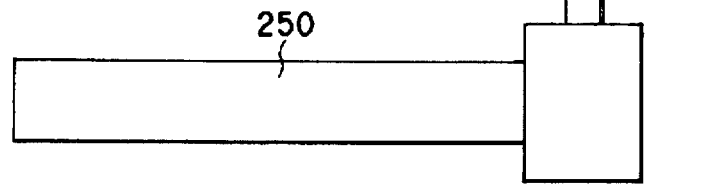
FIG. 14D is a side view of a trocar used in combination with the apparatus illustrated in FIG. 10.
Figure 14E:
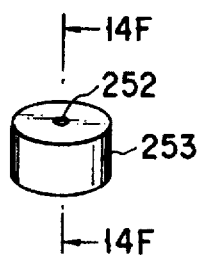
FIG. 14E is a perspective view of a cap used in the apparatus of FIG. 10.
Figure 14F:
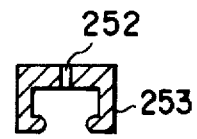
FIG. 14F is a sectional view taken along lien 14F—14F shown in FIG. 14E.

The endoscope apparatus 201 may be used in combination with a trocar 250 which has, as shown in FIG. 14D, has a port 251. Preferably, the port 251 is covered with a cap 253 which has a hole 252 as shown in FIGS. 14E and 14F. The hole 252 has a diameter of about 1 mm. The cap 253 can be made of various materials, such as elastic material (e.g., silicone), plastic material or metal. When the cap 253 is not used to cover the port 251, the cock 254 on the port 251 is half-opened.

How to use the endoscope apparatus 201 will now be explained.

In the case where only the inner tube 213 is used, the insertion section 203 of the main body 202 is inserted into the inner tube 213. The fastening band 233 is connected at one end to one of the hooks 234 provided on the first ring 221. This done, the band 233 is pulled and elongated and is then wrapped around the light-guide connector 207 of the operation section 204. The band 233 is fastened to the other hook 234, with this hook 234 inserted in one of the holes 237 made in the other end portion of the band 233. As a result, the distal end of the insertion section 203 and the inner surface of the inner flange 217 are set in mutual contact. The depressions 219 made in the inner surface of the inner flange 217 therefore define the openings 219a. The openings 219a communicate with the first passage 215, for applying liquid onto the distal end of the insertion section 203 and drawing the liquid back into the first passage 215.

Next, the syringe 227 is connected to the tubular cap 226, either directly or by the extension tube 228. Alternatively, the valve device 229a is connected to the cap 226, either directly or by the tube 229.

If the distal end of the insertion section 203 gets dirty while the apparatus is used to examine the interior of a body cavity, the syringe 227 is pushed, or the valve device 229a is operated, connecting the water-supply unit 229b to the tubular port 226. Physiological saline is thereby supplied from the syringe 227 or the water-supply unit 229b into the first passage 215 through the tubular cap 226. The physiological saline flows to the depressions 219 made in the inner flange 217. It is then applied via the openings 219a onto the distal end of the insertion section 203, washing down the dirt therefrom.

After the distal end of the insertion section 203 has been thus washed, the piston of the syringe 227 is pulled, or the valve device 229a is operated, connecting the suction unit 229c to the tabular cap 226. A negative pressure is thereby generated in the first passage 215. The the used physiological saline and the dirt removed from the distal end of the insertion section 203 are drawn into the first passage 221 and ultimately into the syringe 227 or the suction unit 229c.

In the case where both the inner tube 213 and the outer tube 214, the insertion section 203 is inserted into the inner tube 213. Then, the insertion section 203 with the tube 213 mounted on it is inserted into the outer tube 214 such that the projections 235 on the second ring 222 are aligned with the hooks 234 provided on the first ring 221. Then, the first hook 234 and the first projection 235 aligned together are inserted into the hole 236 of the fastening band 233. This done, the band 233 is pulled and elongated and is wrapped around the light-guide connector 207 of the operation section 204. The second hook 234 and the second projection 235 aligned together are inserted into one of the holes 237 made in the other end portion of the band 233. As a result, the inner tube 213 and the outer tube 214 are simultaneously secured to the main body 202.

At this time, the distal end of the insertion section 203 and the inner surface of the inner flange 217 contact each other. The depressions 219 in the inner surface of the inner flange 217 therefore define the openings 219a which communicate with the first passage 215 to apply liquid onto the distal end of the insertion section 203 and draw the liquid back into the first passage 215. Furthermore, there is provided a space between the outer surface of the inner flange 217 and the inner surface of the outer flange 218. This space serves as a gas-supply port 220 which communicates with the second passage 216.

The distal end of the insertion section 203 may become dirty while the apparatus is used to examine the interior of a body cavity. If so, the syringe 227 is pushed, or the valve device 229a is operated, in the same way as described above, thereby to wash the distal end with physiological saline and draw the used saline and the dirt into the syringe 227 or the suction device 229c.

Dew may be formed on the cover glass provided at the distal end of the insertion section 203, fogging the cover glass and impairing the view clearness of the endoscope. If this is the case, the pneumoperitoneal device 232 connected to the tubular cap 230 by the connecting tube 231 is driven. The device 232 supplies gas into the second passage 216 through the tube 231 and the tubular cap 230. The gas flows through the second passage 216 into the space between the outer surface of the inner flange 217 and the inner surface of the outer flange 218. The gas is applied from the gas-supply port 220 onto the distal end of the insertion section 203, eliminating the fogging on the cover glass.

Usually, a pneumoperitoneal gas is supplied via the port 251 of the trocar 250. The gas can be supplied though the second passage 216, as well. This is because, as mentioned above, the tubular cap 230 is connected by the connecting tube 231 to the pneumoperitoneal device 232. The pneumoperitoneal device 232 stops supplying the gas when the gas pressure in the body cavity reaches to a predetermined value. As indicated above, the cock 254 is half-opened, releasing the gas from the body cavity and enabling the device 232 to supply the gas continuously into the body cavity. If the cock 254 is excessively opened, the gas pressure in the body cavity will be too low, making it difficult to secure a sufficiently wide view field. If the cock 254 is insufficiently opened, the gas pressure in the body cavity will become nearly equal to the predetermined value, and the pneumoperitoneal gas will flow into the cavity only intermittently. In either case, the opening of the cock 254 must be adjusted. To make it unnecessary to adjust the opening of the cock 254, the cap 253 is attached to the port 251 of the trocar 250 to releases the pneumoperitoneal gas through the hole 252 at a specific rate. The device 232 therefore supplies the gas continuously into the body cavity, thus eliminating fogging, if any, on the distal end of the insertion section 203.

The endoscope apparatus 201, i.e., the twelfth embodiment of this invention, is advantageous in the following respects.

When the outer unit 205 is attached to the main body 202, there are automatically formed the first passage 215 between the inner tube 213 of the insertion section 203, and the second passage 216 between the inner tube 213 and the outer tube 214. The first passage 215 and the second passage 216 are independent of each other, not connected at all. Hence, a liquid can be applied through the first passage 215 onto the distal end of the insertion section 203 to wash down dirt (e.g., blood or the like) therefrom, and the dirt and the used liquid can be drawn from the body cavity into the suction unit 229c the first passage 215.

Further, a pneumoperitoneal gas can be supplied from the pneumoperitoneal device 232 to the distal end of the insertion section 203 through the second passage 216, and can then be applied onto the distal end of the insertion section 203 through the gas-supply port 220 which is a space provided between the outer surface of the inner flange 217 and the inner surface of the outer flange 218. The gas applied blows dews away from the distal end of the insertion section 203, easily eliminating the fogging on the distal end of the insertion section 203. Hence, a clear view is secured throughout the use of the endoscope apparatus 201, without pulling the insertion section 203 from the body cavity. This helps to shorten the time of an endoscope operation.

In the case where the pneumoperitoneal device 232 need not be used (that is, the outer tube 214 is unnecessary), only the inner tube 213 can be secured to the main body 202 by using the fastening band 233 and the hooks 234 of the first ring 221. In the case where the inner tube 213 needs to be covered with the outer tube 214, both tubes 213 and 214 can be secured to the main body 202 by inserting the hooks 234 and the projections of the second ring 222 into the holes of the fastening band 223. Since the hooks 234 extend outward beyond the projections 235, they can prevent the rings 221 and 222 from rotating relative to each other.

Moreover, since the fastening band 233 has a plurality of holes 237 in one end portion, it can serve to fasten the inner tube 213 to the main body 202, regardless of the position which the light-guide connector 207 assumes with respect to the outer unit 205.

As described above, the tubular cap 226 formed integral with the first ring 221 and the tubular cap 230 connected to the second ring 222 extend slantwise with respect to the axis of the outer unit 205. Therefore, the tubular components (i.e., the syringe 227, the tube 229 and the tube 229) connected to the caps 226 and 229 also extend slantwise and are less likely to entangle than otherwise. In addition, since the tubular caps 226 and 230 have different shapes, a wrong tube cannot be connected to either cap.

The second passage 216 has a cross section of 1 mm² to 40 mm². The cross section is large enough to allow the device 232 to supply the pneumoperitoneal gas at a high rate to accomplish pneumoperitoneal treatment. Since the pneumoperitoneal gas can be supplied into the body cavity through the second passage 216, no tube need not be provided for supplying the gas into the body cavity. Hence, the endoscope apparatus 201 has a relatively small number of tubes.

As indicated above, the cap 253 having the hole 252 is attached to the port 251 of the trocar 250 and releases the pneumoperitoneal gas at a specific rate. The device 232 supplies the gas into the body cavity, compensating for the gas released. The rate at which the gas is released through the hole 252 is virtually equal to the rate at which the device 232 supplies the gas into the body cavity. The pneumoperitoneal device 232 can continuously supplies the gas into the body cavity. This prevents the gas pressure in the body cavity from lowering, and the distal end of the insertion section 203 from being fogged during the use of the endoscope apparatus 201.

Figure 15:
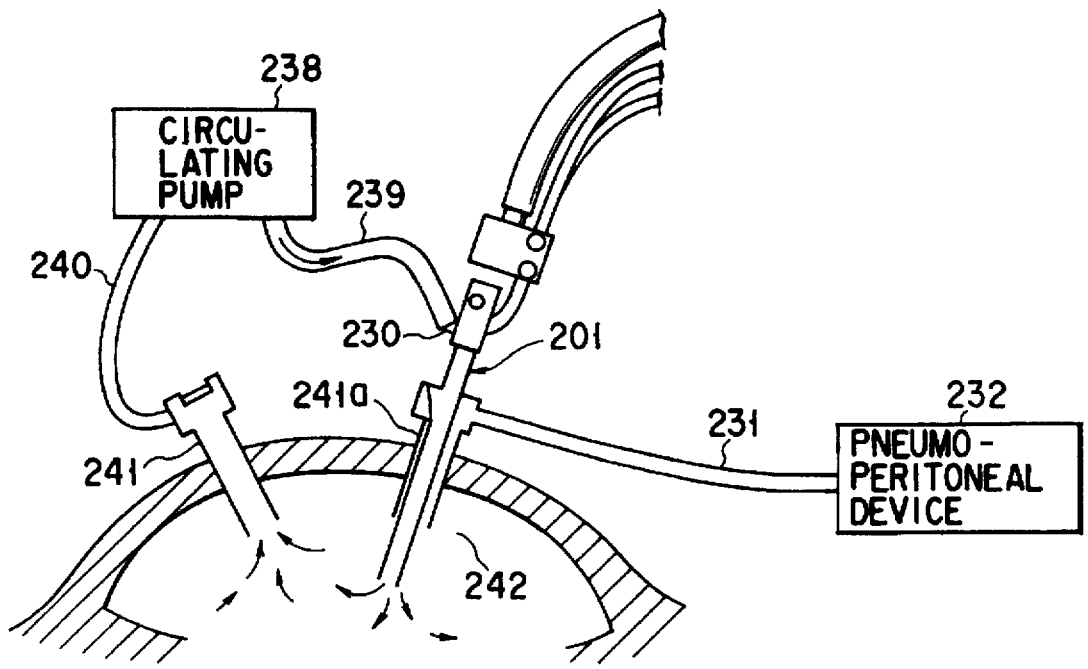
FIG. 15 is a view explaining how the endoscope apparatus according to a thirteenth embodiment of the invention is used.

FIG. 15 shows an endoscope apparatus 201 according to the thirteenth embodiment of the present invention.

This apparatus 201 differs the twelfth embodiment in that a circulating pump 238, e.g., a roller pump, is used to supply gas to the distal end of the insertion section 203 in order to prevent fogging on the distal end. The pump 238 is connected to the tubular cap 230 of the endoscope apparatus 201 by a gas-supplying tube 239, and also to a first trocar 241 by a suction tube 240. To perform a pneumoperitoneal treatment in a body cavity 242, a pneumoperitoneal device 232 is connected to a second trocar 241a.

In operation, the circulating 238 is driven, drawing the pneumoperitoneal gas from the body cavity 242. The gas passes first through the gas-supplying tube 239 and then through the endoscope apparatus 201. It is applied onto the distal end of the apparatus 201, thereby eliminating fogging on the distal end. As can be understood from FIG. 15, the pneumoperitoneal gas flows in a circuit comprises of the endoscope 201, the tube 239, the pump 238, the tube 240, the first trocar 241 and the body cavity 242. The pneumoperitoneal gas can therefore be saved.

Figure 16:
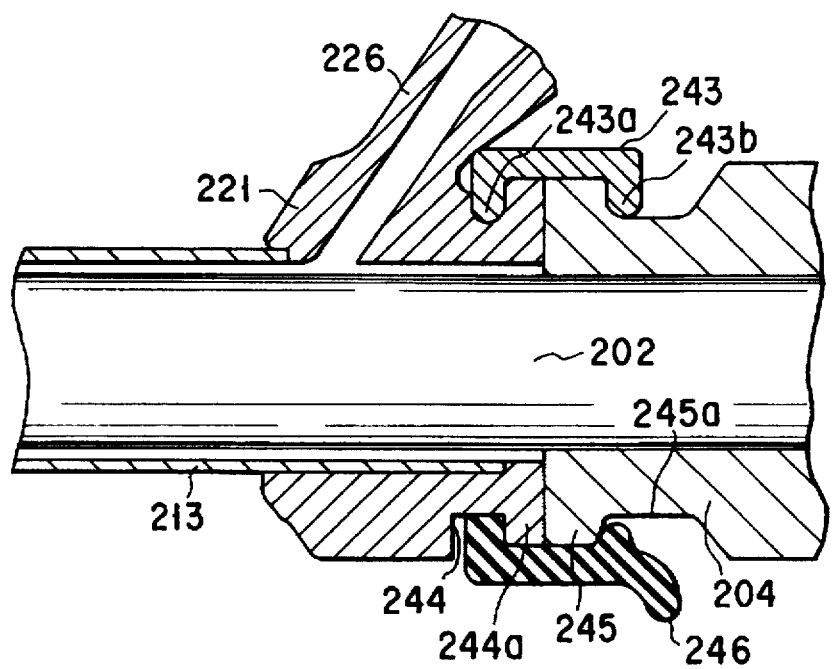
FIG. 16 is a longitudinal sectional view showing a part of an endoscope apparatus according to a fourteenth embodiment of the present invention.

FIG. 16 illustrates a part of an endoscope apparatus according to the fourteenth embodiment of the present invention. This apparatus is identical to the twelfth embodiment, except that a fastening ring 243 is used in place of the fastening band 233.

As shown in FIG. 16, the first ring 221 has an annular groove 244 formed in the outer circumferential surface of its rear end. Similarly, the operation section 204 has an annular groove 245a formed in the outer circumferential surface of its distal end. As a result of this, the first ring 221 has a flange 244a at its rear end, and the operation section 204 has a flange 245 at its front end. The rear end of the first ring 221 and the front end of the operation section 204 have substantially the same diameter. Therefore, the flanges 244a and 245 have substantially the same diameter.

The fastening ring 243 is provided at the junction between the flange 244a of the first ring 221 and the flange 245 of the second ring 222. The ring 243 has a U-shaped cross section. It has has two annular projections 243a and 243b. The front annular projection 243a is fitted not removably in the annular groove 244 of the first ring 221, whereas the rear annular projection 243b is removably fitted in the annular groove 245a of the operation section 204. Thus, the first ring 221 is fastened by the ring 243 to the operation section 204 of the main body 202. It is desirable that the fastening ring 232 be made of plastic material such as silicone so that it may keep pulling the first ring 221 and the operation section 204 to each other. The fastening ring 243 has a tab 246 which can be pinched with the thumb and the forefinger, facilitating the removal of the ring 243 from the junction between the flanges 244a and 245. The annular grooves 244 and 245a have an outer diameter greater than the diameter of the annular projections 243a and 243b of the fastening ring 243.

The first ring 221 is fastened to the operation section 204 in the following procedure. First, the insertion section 203 is inserted into the inner tube 213. Next, the tab 246 of the fastening ring 243 is held and pulled outwards, expanding the rear end of the ring 243, and the front end of the operation section 204 is inserted into the fastening ring 243. Then, the tab 246 is released, thus fitting the rear annular projection 243b into the annular groove 245a of the operation section 204. Since the fastening ring 243 is made of elastic material, the flange 217 of the inner tube 213 and the flange 218 of the outer tube 214 firmly contact the distal end of the insertion section 203.

Since its annular projections 243a and 243b have a smaller diameter than the annular grooves 244 and 245a, the fastening ring 243 clamps both the rear end of the first ring 221 and the front end of the operation section 204. The ring 243 can therefore fasten the first ring 221 and the operation section 294 in watertight and airtight fashion, without using any seal. No component equivalent to the seal 223 used in the twelfth embodiment is necessary at all.

Made of elastic material such as silicone, the fastening ring 243 can steadily fasten the first ring 221 to the operation section 204 even if the insertion section 203 is somewhat longer or shorter than the desired length. In addition, since the flanges 217 and 218 firmly contact the distal end of the insertion section 203 due to the elasticity of the fastening ring 243, the liquid-supplying openings 219a and the gas-supply port 220 retain their shapes all the time the endoscope apparatus 201 is used. Liquid and gas can therefore be smoothly supplied to the distal end of the insertion section 203 and smoothly drawn therefrom.

FIGS. 17 to 20 show a first modified valve device which can be utilized in an endoscope apparatus according to the present invention to control the supplying and drawing liquid and gas.

Valve devices of various types are known as is disclosed in Jpn. Pat. Appln. KOKOKU Publication No. 3-28213 and Jpn. Pat. Appln. KOKAI Publication No. 4-231023. Each of these devices comprises a cylinder, a piston inserted in the cylinder, and at least two tubes connected to the cylinder. The piston can be moved back and forth in the cylinder so that one of the tubes communicates with the interior of the cylinder.

A valve device may have two or more cylinders arranged side by side, with their inlet ends juxtaposed and their outlet ends juxtaposed. In this case there will arise a problem. Since any tube connected to one cylinder must pass around any other cylinder, a considerable number of tubes must be connected to the housing of the valve device, and the tubes must be bent in the housing. The valve device is inevitably complex in structure. It follows that the device cannot be manufactured at low cost and cannot be washed with ease.

The inventors hereof have developed a modified valve device which has a simple structure, which can therefore be made at low cost and is easy to wash, though it has two or more cylinders arranged side by side, with their inlet ends juxtaposed and their outlet ends juxtaposed.

Figure 19:
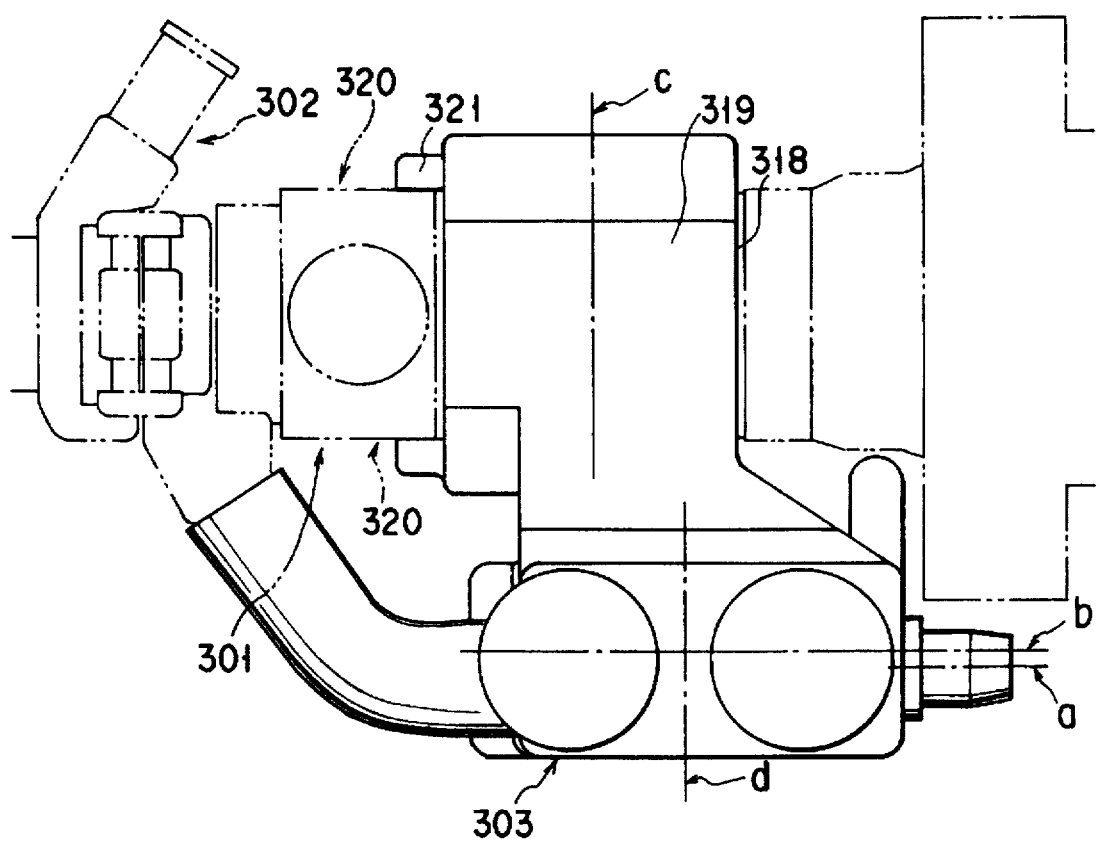
FIG. 19 is a plan view of the first modified valve device.
Figure 20:
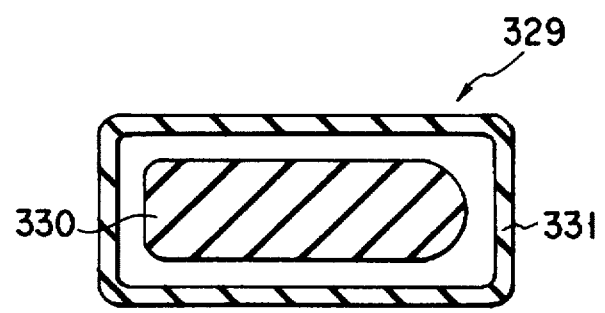
FIG. 20 is a cross-sectional view of the cap of the first modified valve device.

FIG. 17 is a longitudinal sectional view of the modified valve device 303, FIG. 18 is a cross-sectional view of the device 303, FIG. 19 is a plan view of the device 303, and FIG. 20 is a cross-sectional view of the cap the device 303 has.

As shown in FIG. 19, the valve device 303 is used in combination with an endoscope 301 and an outer unit 302 mounted on the endoscope 301. In FIGS. 17 and 19, the insertion section of the endoscope 301 is illustrated in the left side. In FIG. 18, "R" is the rear of the main body 304 of the valve device 303, and "F" is the front of the main body 304.

The main body 304 of the device 303 is generally a rectangular block made of synthetic resin or rigid material such as metal. Two cylinders 305 and 306 are provided in the main body 304. More precisely, the first cylinder 305 is located in the distal end portion, and the second cylinder 306 in the proximal end portion. The upper portion 307a of the first cylinder 305 has a smaller diameter than the lower portion 308a. Similarly, the upper portion 307b of the second cylinder 306 has a smaller diameter than the lower portion 308b. The lower portion 308a of the first cylinder 305 has a circular cross section, whereas the lower portion 308b of the second cylinder 306 has a square cross section, each side of which is equal to the diameter of the lower portion 308a of the first cylinder 305.

A hollow cylindrical button-holder 309 is formed integral with the main body 304, located on the upper end of the first cylinder 305 and axially aligned therewith. Similarly, a hollow cylindrical button-holder 309 is formed integral with the main body 304, located on the upper end of the second cylinder 306 and axially aligned therewith. Either button-holder 309 has a thick rim 310. A passage 311 is formed within the main body 304, connecting the bottoms of the cylinders 305 and 306.

Two inlet ports 312 and 313 are formed in the rear R of the main body 304. The inlet ports 312 and 313 communi- cate with the lower portion 308a of the first cylinder 305 and the lower portion 308b of the second cylinder 306, respectively—with their axes intersecting with the axes of the cylinders 305 and 306. As seen from FIG. 19, the axis a of the first inlet port 312 is slightly set off from the axis b of the main body 304 toward the front F of the main body 304, and the second inlet port 323 is spaced upwards from the first inlet port 312 by an appropriate distance. As shown in FIG. 17, two tubular caps 314 protrude from the rear R of the main body 304, axially aligned with the axes of the inlet ports 312 and 313, respectively. Tubes (not shown) can be connected to these tubular caps 314.

As shown in FIG. 17, an outlet port 315 is formed in the front F of the main body 304, extending at right angles to the axes of the cylinders 305 and 306. The outlet port 315 passes through the upper portion 307a of the first cylinder 305, reaching the upper portion 307b of the second cylinder 306. A tubular cap 316 protrudes from the main body 304 and axially aligned with the outlet port 315. A tube (not shown) can be connected to this tubular cap 316.

The lower end portion of the main body 304 is less broad than the other portion. An annular projection 317 is mounted on the lower end of the main body 304, flush with the bottom of the main body 304. As shown in FIG. 18, a C-shaped arm 319 protrudes from the rear R of the main body 304. The arm 319 has an inner diameter virtually equal to the outer diameter of the operation section of the endoscope 301. The arm 319 has a slit in its lower part. As illustrated in FIG. 19, the axis c of the arm 319 extends at right angles to the axis of the endoscope 301 and is slightly set off toward the distal end of the endoscope 301 from the axis d of the main body 304 which also extends at right angles to the axis of the endoscope 301. A pair of stoppers 321 protrude forward from the arm 319, spaced apart from each other by a distance nearly equal to a portion 320 of the endoscope 301.

As FIG. 17 shows, a first button 325 is slidably fitted in the first cylinder 395, and a second button 326 is slidably fitted in the second cylinder 396. The buttons 325 and 326 have a shaft 323 each. The shaft 323 has a valve body 324 at its lower end. The upper end portion of each shaft 323 projects out of the cylinder and has an annular groove in its outer circumferential surface. Fitted in this annular groove is the upper end 328 of a hollow cylindrical rubber spring 322, whose lower end 327 is fitted in the annular groove defined by the thick rim 310 of the button-holder 309 and the top surface of the main body 304. The lower end 327 of each rubber spring 322 has an inner diameter slightly less than the outer diameter of the annular groove defined by the rim 310 and the top of the main body 304. The upper end 328 of each spring 322 has an inner diameter slightly less than the outer diameter of the annular groove formed in the upper end portion of each shaft 323. Hence, either rubber spring 322 achieves airtight sealing between the cylinder (306 or 306) and the button (325 or 326).

The shafts 323 have such a length that the valve bodies 324 may have its stroke midpoint substantially at the junction between the upper portion 307b and lower portion 308b of the second cylinder 306.

A cap 329 is removably attached to the lower end of the main body 304, closing the passage 311 which would otherwise be opened. The cap 329 is made of elastic material such as silicone rubber, fluororubber or the like. The cap 329 has a bottom plate 330 having an appropriate thickness. The plate 330 has an annular projection 331 fitted in the annular groove made in the outer circumferential surface of the lower end of the main body 304. The plate 330 closes the lower end of the main body 304. A columnar member 332 protrudes upward from the inner surface of the bottom plate 330 and is fitted in the lower portion 308a of the second cylinder 306. The columnar member 332 has a neck portion 333 and a seal portion 334. The neck portion 333 has a diameter smaller than the inner diameter of the lower portion 308b of the second cylinder 306, and functions as a passage means. The seal portion 334 is located between the inlet ports 312 and 313 and provides airtight sealing between the first inlet port 312 and the lower portion 308b of the second cylinder 306.

The operation of the valve device 303 will now be described in detail.

A first fluid flows via the first inlet port 313 into the second cylinder 306, passes through the space between the second cylinder 306 and the neck portion 333, and flows into the first cylinder 305. When the first button 325 is pushed, the valve body 324 is moved from the upper portion 307a (i.e., narrow portion) of the first cylinder 305 to the lower portion 308a (i.e., broad portion) of the first cylinder 305, providing a space between the first cylinder 305 and the valve body 324. Through this space the first fluid flows to the outlet port 315. When the first button 325 is released, the valve body 324 returns to its initial position by virtue of the force of the rubber spring 322, stopping the flow of the first fluid.

Similarly, a second fluid flows via the first inlet port 313 into the second cylinder 306. When the second button 326 is pushed, the valve body 324 is moved from the upper portion 307b (i.e., narrow portion) of the second cylinder 306 to the lower portion 308b (i.e., the broad portion) of the second cylinder 306, providing a space between the second cylinder 306 and the valve body 324. The second fluid flows through this space into the outlet port 315. When the second button 326 is released, the valve body 324 returns to its initial position by virtue of the force of the rubber spring 322, stopping the flow of the fluid.

With the valve device 303 it is possible to control the supply of one fluid and the supply of another fluid, independently.

Since either fluid is made to flow into the outlet port 315 when the valve body 324 is moved from the upper portion to the lower portion of the cylinder. Hence, the first button 325 and the second button 326 can be of the same type despite the first inlet port 312 and the second inlet port 313 are arranged side by side in the axial direction of the cylinders 305 and 306.

As described above, the main body 304 of the valve device 303 is set off rearward with respect to the arm 319. The tubular cap 316 can therefore be more spaced greatly from the outer unit 302 mounted on the endoscope 301. This renders it easy to connect tubes to the cap 316 and to the outer unit 302. Further, since the tubular caps 314 and 316 are set off toward the front F with respect to the axis b of the main body 304 toward, the tubes connected to the valve device 303 do not bother a person operating the endoscope 301.

The lower portion 308a of the first cylinder 305 and the lower portion 308b of the second cylinder 306 may have different cross-section shapes, and the cap 329 removably attached to the lower end of the main body 304 may be so formed to fit, at two portions, in the lower portions 308a and 308b. This will facilitate the assembling of the valve device 303, preventing erroneous arranging of the parts.

The stoppers 321 protruding forward from the arm 319 not only help to attach the valve device 303 to the endoscope 301, but also prevents the device 303 from rotating with respect to the endoscope 301. The cap 329 removably attached to the lower end of the main body 304 may be formed integral with a tube 340 which connects the outer unit 302 and the valve device 303. If so, the number of components will be reduced, ultimately decreasing the manufacturing cost of the valve device 303. Further, it will be less possible that the cap 329 or the tube 340 is lost after the device 303 has been overhauled for washing.

Figure 21:
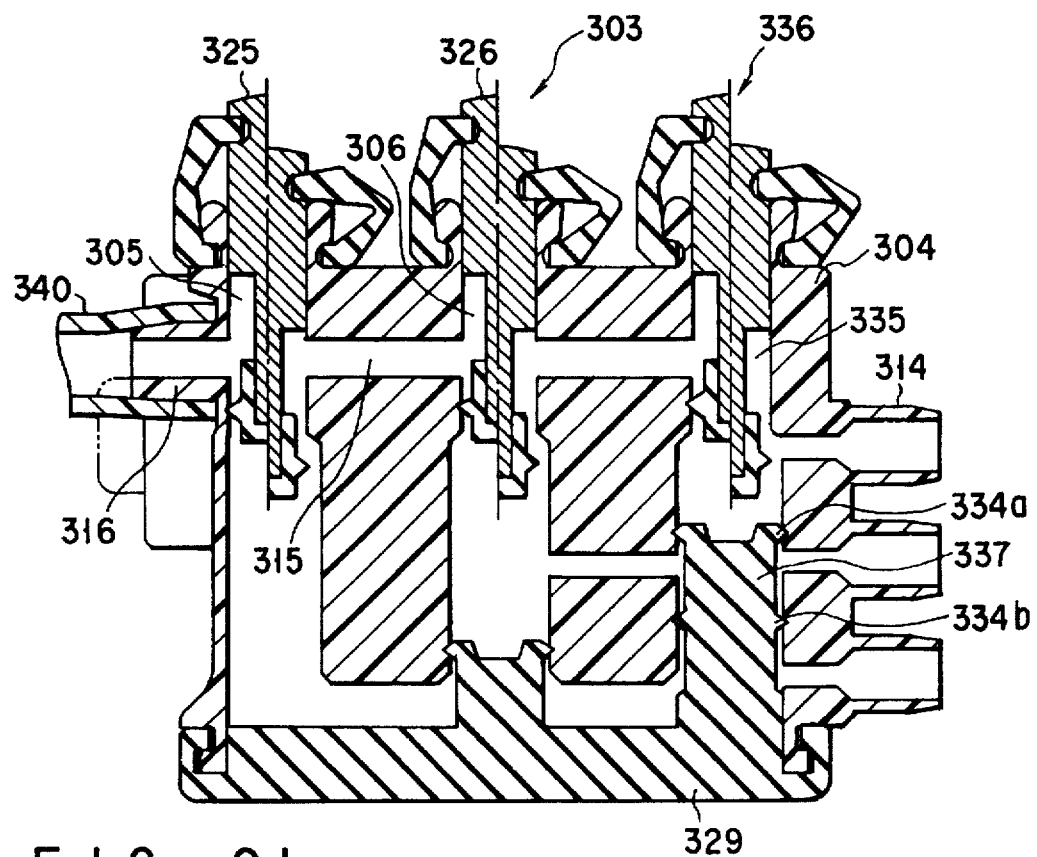
FIG. 21 is a longitudinal sectional view of a second modified valve device.

The number of cylinders incorporated in the valve device 303 is not limited to two, i.e., the number of different fluids the flow of which is controlled by operating the valve device 303. Rather, as in the case of the second modified valve device shown in FIG. 21, a third cylinder 335 may be used in addition to the first cylinder 305 and the second cylinder 306. The second modified valve device has a third button 336 inserted in the third cylinder 335, in addition to the buttons 325 and 326 inserted in the cylinders 305 and 306, respectively. The second modified valve device further has a third tubular cap 314 connected to the main body 304 and located above the second inlet port 313. The columnar member 337 has two seals 334a and 334b, which are positioned at a height between the second and third inlet ports 313 and 314 and a height between the first and second inlet port 312, respectively.

Figure 22:
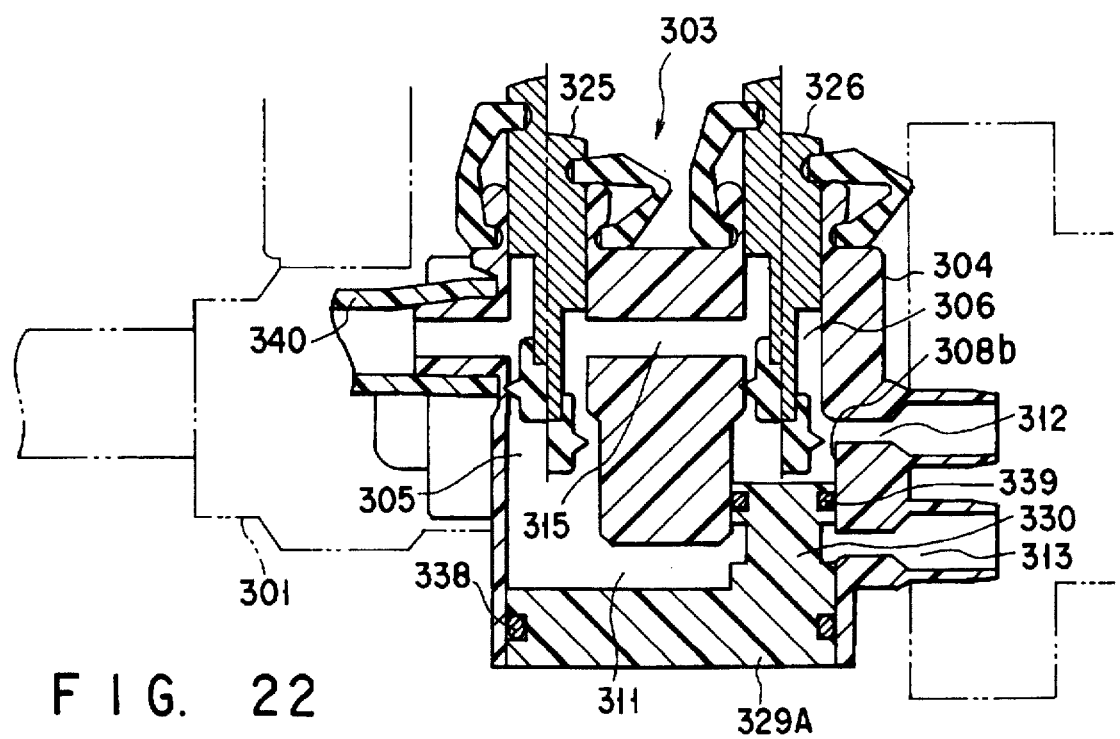
FIG. 22 is a longitudinal sectional view of a third modified valve device.

The cap 329 is not limited to a single-piece component made of rubber. Rather, as in the case of the third modified valve device shown in FIG. 22, the cap 329 may be a three-piece one comprising a main body 329A, a first seal 338 and a second seal 339. The main body 329A is made of resin or metal and consists of a lower portion and a upper portion. The first seal 338 is fitted in a groove formed in the circumferential surface of the main body 329a. The second seal 339 is fitted in an annular groove made in the circumferential surface of the upper end portion of the main body 329A and achieves airtight sealing between the upper and lower portions 307b and 308b of the second cylinder 306.

The cap 329 may be formed integral with a tube 340 which connects the outer unit 302 and the valve device 303.

Figure 23:
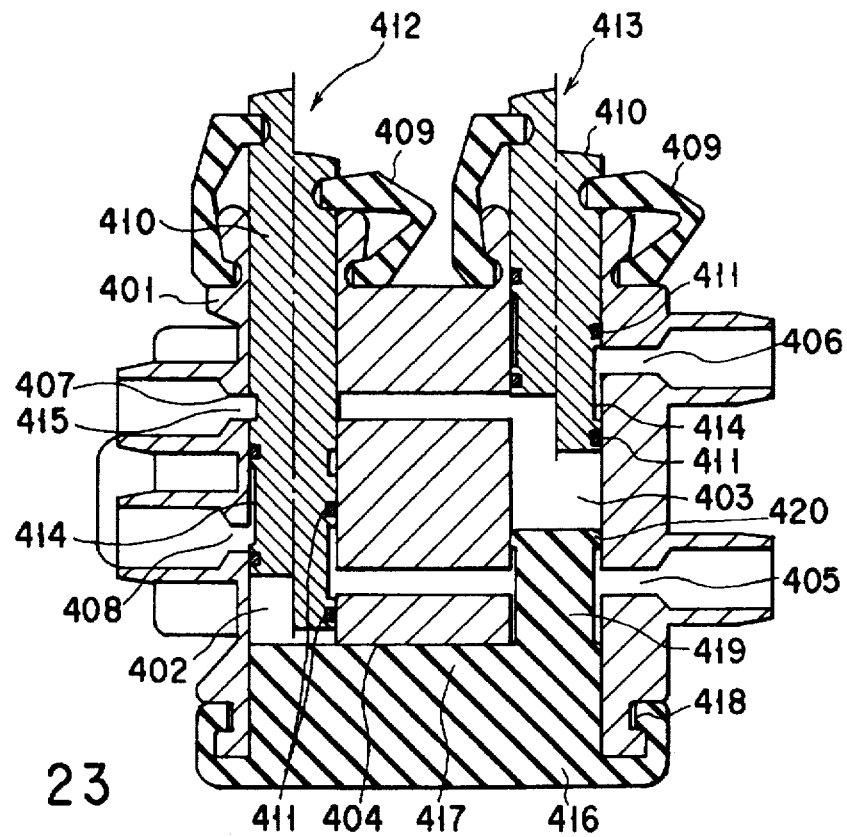
FIG. 23 is a longitudinal sectional view of a fourth modified valve device.

FIG. 23 shows a fourth modified valve device. This modified valve device comprises a main body 401 and has two cylinders 402 and 403. The main body 401 is is a substantially rectangular block. The first cylinder 402 and the second cylinder 403 are formed in the front and rear halves of the main body 401, respectively. A passage 404 having a rectangular cross section is provided in the lower part of the main body 401. The passage 404 has a width equal to the diameter of either cylinder and connects the cylinders 402 and 403.

Two inlet ports 405 and 406 are provided on the rear side of the main body 401. The first inlet port 405 extends at right angles to the axis of the first cylinder 402, passing through the second cylinder 403 and communicating with the first cylinder 402. The second inlet port 406 is located above the first inlet port 405 and spaced apart therefrom by a proper distance. The second inlet port 406 communicates with the second cylinder 403.

A second outlet port 407 and a first outlet port 408 are provided on the front side of the main body 401. The second outlet port 407 extends at right angles to the axis of the second cylinder 403, passing through the first cylinder 402 and communicating with to the second cylinder 403. The first outlet port 408 is located below the second outlet port 407 and spaced apart therefrom by an appropriate distance. The first outlet port 408 communicates with the second cylinder 403.

The fourth modified valve device further comprises two buttons 412 and 413 and two rubber springs 409. The buttons 412 and 413 are inserted in part in the first cylinder 402 and the second cylinder 403, respectively. The buttons 412 an 413 have a shaft 410 each. Each rubber spring 409 is connected at one end to the main body 401 and at the other end to the corresponding button, in the same way as in the first modified valve device illustrated in FIG. 17. Two ring seals 411 are fitted in two annular grooves cut in the circumferential surface of the lower portion of either shaft 410.

The shafts 410 have a diameter a little smaller than the diameter of the cylinders 402 and 403. The shaft 410 of the second button 413 has such a length that the lower seal 411 remains at the midpoint between the first inlet port 406 and the second outlet port 407 as long as the first button 413 is held at its upper position by virtue of the force of the rubber spring 409. On the other hand, the shaft 410 of the first button 412 has such a length that the lower seal 411 stays at the midpoint between the first inlet port 405 and the first outlet port 408 as long as the first button 412 is held at its upper position by virtue of the force of the rubber spring 409.

Each shaft 410 has a neck portion 414, which is located between the upper and lower seals 411 and which has a diameter smaller by a proper value than that of the cylinders 402 and 403. The neck portion 414 has a length which is substantially equal to the sum of the inner diameter of the first inlet port 405, the inner diameter of the second outlet port 406 and the distance between these ports 405 and 406. The shaft 410 of the first button 412 has another neck portion 415, which is located at the second outlet port 407. The neck portion 415 has a diameter smaller than the inner diameter of the first cylinder 402 and a length substantially equal to the inner diameter of the second outlet port 407.

A cap 416 is removably attached to the lower end of the main body 401 which is made of elastic material such as rubber. The cap 416 has a bottom plate 417 fitted in the hollow made in the lower portion of the main body 401, defining the bottom of the passage 404. The plate 417 has having an appropriate thickness and the same shape as the hollow. The bottom plate 417 has an annular projection 418 fitted in the annular groove made in the outer circumferential surface of the lower end of the main body 401. The plate 417 closes the lower end of the main body 401. A columnar member 419 protrudes upward from the inner surface of the bottom plate 417 and is fitted in the lower portion of the first cylinder 408. The columnar member 419 has an annular seal 420, which is located between the first inlet port 405 and the second inlet port 406.

In operation, a fluid flows via the first inlet port 405 into the first cylinder 402 through a space between the second cylinder 403 and the columnar member 419. When the first button 412 pushed, the seal 411 is moved to a position below the first inlet port 405, providing a space between the first cylinder 402 and the neck portion 414. The fluid flows through this space into the first outlet port 408.

Meanwhile, another fluid flows into the second cylinder 403 through the second inlet port 406. When the second button 413 is pushed, the fluid flows through the space between the first cylinder 402 and the neck portion 414 of the second button 413 and further through the space between the first cylinder 402 and the neck portion 415. As a result, the fluid flows from the valve device through the second outlet port 407. When the second button 413 is released, the seal 411 is moved up to its initial position, by virtue of the force of the rubber spring 409. Then, the fluid can no longer flow to the second outlet port 407.

Figure 24:
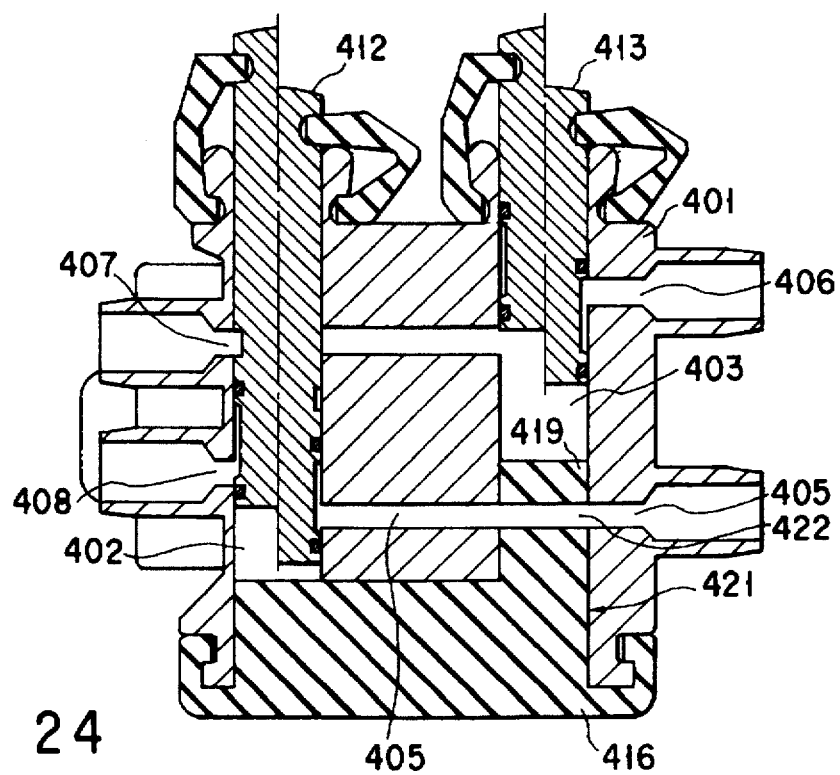
FIG. 24 is a longitudinal sectional view of a fifth modified valve device.

FIG. 24 shows a fifth modified valve device. This valve device differs from the fourth modified valve device (FIG. 23) in three respects. First, the columnar member 419 of the cap 416 has a diameter which is either equal to or a little greater than the inner diameter of the second cylinder 403. Second, that portion of the member 419 which is fitted in the second cylinder 403 serves as a seal 421. Third, said portion of the member 419 has a horizontal hole 422 which connects the first inlet port 405 and the first cylinder 402, and which functions as a passage means. In operation, a fluid flows from the first inlet port 405 into the first cylinder 402 through the horizontal hole 422. Except for this point, the fifth modified valve device operates in the same way as the fourth modified valve device.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A valve device having at least two valve bodies arranged side by side for supplying and drawing water and supplying gas, said device comprising:

a valve body having a tubular cap;

at least two cylinders provided in said valve body, said at least two cylinders each having an open lower end;

a plurality of inlet ports corresponding in number to said at least two cylinders, said inlet ports communicating with a first one of said at least two cylinders, said inlet ports extending substantially perpendicular to an axis of said first one of said at least two cylinders and being spaced apart in an axial direction of said first one of said at least two cylinders;

at least one outlet port communicating with a second one of said at least two cylinders opposing said first one of said at least two cylinders, said second one of said at least two cylinders being connected to said tubular cap of said valve body;

valve means slideably mounted in said at least two cylinders for opening and closing a flow of fluid from at least one of said inlet ports to said at least one outlet port; and one cap removably coupled to said valve body, said one cap including: (i) seal members for closing the open lower ends of said at least two cylinders, respectively, and (ii) at least one partition dividing said first one of said at least two cylinders into one of: (a) a passage and a groove and (b) a passage and a second inlet port.

2. The valve device according to claim 1, wherein said seal members comprise annular seals.

3. The valve device according to claim 1, wherein said cap includes passage means for allowing a fluid to pass through said cylinders.

4. The valve device according to claim 1, wherein said cap comprises a single unit made of elastic material.

5. The valve device according to claim 4, wherein said elastic material comprises silicone rubber.

6. The valve device according to claim 4, wherein said elastic material comprises fluororubber.

7. The valve device according to claim 1, wherein said cap comprises a rigid main body.

8. The valve device according to claim 7, wherein said rigid main body is made of metal.

9. The valve device according to claim 7, wherein said rigid main body is made of synthetic resin.

10. The valve device according to claim 7, wherein said seal member comprises an O-ring.

* * * * *

UNITED STATES PATENT AND TRADEMARK OFFICE
CERTIFICATE OF CORRECTION

PATENT NO. : 5,697,888
DATED : December 16, 1997
INVENTOR(S) : KOBAYASHI et al.

It is certified that error appears in the above-identified patent and that said Letters Patent is hereby corrected as shown below:

Title page, Item [56] References Cited, under "U.S. PATENT DOCUMENTS" insert:
--5,299,561  4/1994  Yoshimoto  600/159
  5,347,992  9/1994  Pearlman   600/159--.

Signed and Sealed this

Twenty-seventh Day of October, 1998

Attest:

BRUCE LEHMAN

Attesting Officer

Commissioner of Patents and Trademarks